US010251593B2

(12) United States Patent
Sugla et al.

(10) Patent No.: US 10,251,593 B2
(45) Date of Patent: Apr. 9, 2019

(54) SYSTEM AND METHOD FOR PREVENTION OF PRESSURE ULCERS

(71) Applicants: Binay Sugla, Holmdel, NJ (US); Benjamin Kwan, Red Bank, NJ (US)

(72) Inventors: Binay Sugla, Holmdel, NJ (US); Benjamin Kwan, Red Bank, NJ (US)

(*) Notice: Subject to any disclaimer, the term of this patent is extended or adjusted under 35 U.S.C. 154(b) by 203 days.

(21) Appl. No.: 15/018,607

(22) Filed: Feb. 8, 2016

(65) Prior Publication Data
US 2016/0228050 A1 Aug. 11, 2016

Related U.S. Application Data
(60) Provisional application No. 62/113,226, filed on Feb. 6, 2015.

(51) Int. Cl.
A61B 5/00 (2006.01)
A61G 7/057 (2006.01)
G06F 19/00 (2018.01)
G08B 7/06 (2006.01)
G08B 25/08 (2006.01)
G08B 25/10 (2006.01)

(52) U.S. Cl.
CPC ............ A61B 5/447 (2013.01); A61B 5/0002 (2013.01); A61G 7/05776 (2013.01); G06F 19/3418 (2013.01); G08B 7/06 (2013.01); G08B 25/08 (2013.01); G08B 25/10 (2013.01); A61B 2562/08 (2013.01); A61G 2203/10 (2013.01); A61G 2203/30 (2013.01); A61G 2203/34 (2013.01); A61G 2203/46 (2013.01)

(58) Field of Classification Search
CPC ............................ A61B 5/447; H61G 2203/34
See application file for complete search history.

(56) References Cited

U.S. PATENT DOCUMENTS 6,287,253 B1 * 9/2001 Ortega ................ A61B 5/0051
128/897
6,951,632 B2 10/2005 Unger et al.
7,359,765 B2 4/2008 Varvarelis et al.
7,397,169 B2 7/2008 Nersessian et al.
(Continued)

Primary Examiner — George R Evanisko
(74) Attorney, Agent, or Firm — Young Basile Hanlon & MacFarlane, P.C.

(57) ABSTRACT

A method and system for monitoring and preventing a patient from developing pressure ulcers, comprising (1) a sensing unit, which includes a pressure sensor, attachable to a body part of a patient and having a unique identifier, for detecting pressure exerted by a supporting surface and outputting pressure data indicative of pressure as a function of time; and a wireless transceiver for transmitting the pressure data and/or the unique identifier; (2) a controller unit configured for receiving the pressure data and the unique identifier, associating the unique identifier with the body part of the patient, and for transmitting the pressure data and the unique identifier; and (3) a central server device configured for (i) receiving the unique identifier and the pressure data from the controller unit; (ii) determining whether the pressure data exceeds a predetermined value associated with the body part of the patient; and (iii) transmitting to the controller unit a determination that the pressure data exceeded the predetermined value, the controller unit outputting a signal indicative of the determination.

15 Claims, 16 Drawing Sheets

(56) References Cited

U.S. PATENT DOCUMENTS

| | | | |
|---|---|---|---|
| 7,470,547 B2 | 12/2008 | Tisone et al. | |
| 8,011,041 B2 | 9/2011 | Hann | |
| 8,431,264 B2 | 4/2013 | Neudecker et al. | |
| 8,675,059 B2 | 3/2014 | Johnson et al. | |
| 9,833,194 B2 * | 12/2017 | Hayes | A61B 5/6892 |
| 2005/0057123 A1 | 3/2005 | Deng | |
| 2005/0165284 A1 | 7/2005 | Gefen | |
| 2005/0172398 A1 * | 8/2005 | Smith | A61G 5/1043 |
| | | | 5/81.1 R |
| 2006/0085919 A1 * | 4/2006 | Kramer | A47C 7/022 |
| | | | 5/713 |
| 2007/0056101 A1 | 3/2007 | Mahajan et al. | |
| 2008/0278336 A1 * | 11/2008 | Ortega | A61B 5/1113 |
| | | | 340/573.5 |
| 2009/0143703 A1 * | 6/2009 | Dixon | A61B 5/1115 |
| | | | 600/587 |
| 2011/0068939 A1 * | 3/2011 | Lachenbruch | A61B 5/002 |
| | | | 340/626 |
| 2011/0239370 A1 | 10/2011 | Turo et al. | |
| 2011/0263950 A1 * | 10/2011 | Larson | A61B 5/024 |
| | | | 600/301 |
| 2012/0078144 A1 | 3/2012 | Sinykin | |
| 2012/0086285 A1 | 4/2012 | Hyoung et al. | |
| 2013/0006151 A1 | 1/2013 | Main et al. | |
| 2013/0090571 A1 | 4/2013 | Nourani et al. | |
| 2013/0281804 A1 * | 10/2013 | Lee | A61B 5/447 |
| | | | 600/324 |
| 2013/0310696 A1 | 11/2013 | Ribble et al. | |
| 2016/0135731 A1 * | 5/2016 | Drennan | A61B 5/0004 |
| | | | 600/587 |
| 2016/0256100 A1 * | 9/2016 | Jacofsky | A47C 31/123 |

\* cited by examiner

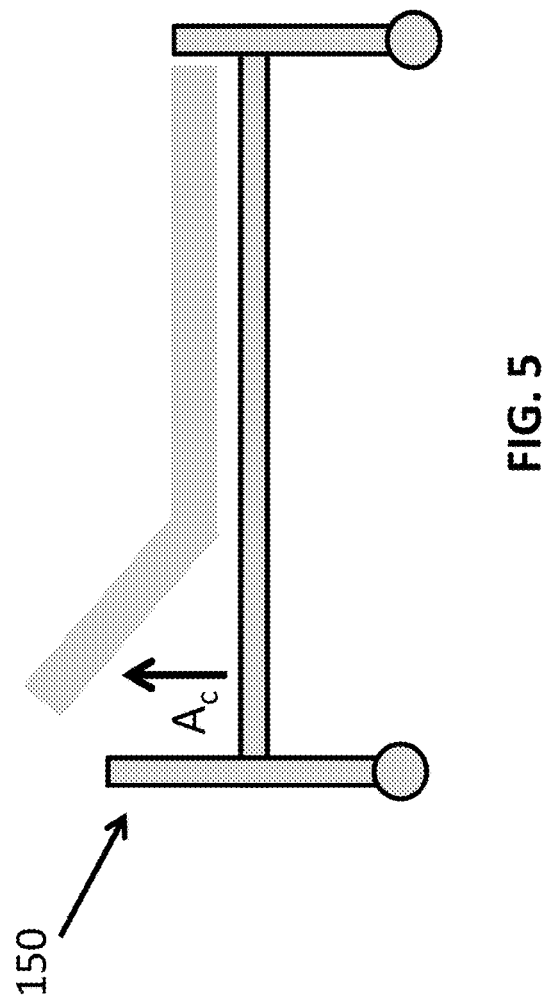

SYSTEM AND METHOD FOR PREVENTION OF PRESSURE ULCERS

CROSS REFERENCE TO RELATED APPLICATIONS

This application claims priority to U.S. Provisional Application No. 62/113,226 filed on Feb. 6, 2015.

FIELD OF INVENTION

This invention relates to the prevention of pressure ulcers and, more particularly, to the real-time monitoring and prevention of the formation of pressure ulcers on a patient.

BACKGROUND OF THE INVENTION

Pressure ulcers are formed when one or more parts of the body are subjected to prolonged pressure. Pressure ulcers and related medical conditions such as pressure induced ischemia are a serious health hazard for patients who are prone to stay in the same or substantially the same posture in bed/chair or any other surface for an extended amount of time subjecting parts of their bodies to sustained pressure. These pressure ulcers, if left undetected, can potentially cause infection that may be life threatening, and complicated and expensive to treat. Besides the human costs, the economic loss is in billions of dollars for USA alone. It is therefore imperative to find much more effective solutions to help prevent pressure ulcers.

The current prevalent method for preventing Pressure Ulcers is largely manual in that patients change their position through their own efforts or with help from the caregiver at periodic intervals. For example, the current guidelines recommend that patients be turned every two hours by default. However, this method has not worked well in practice as busy caregivers often forget to turn the patient. Also, sometimes the patient may inadvertently revert to a position which could cause harm. In order to improve this prevention process, several solutions have been suggested and offered on the market.

The solutions that have been proposed and/or built fall into two distinct classes. At the outset, it is important to point out that prior art for both classes of system uses simple pressure sensing units that have no inbuilt intelligence. The first class of solutions attempt to estimate the pressure on the various body parts or limbs indirectly. These methods as described in U.S. Patent No. 2013/0090571 include measuring the pressure at various points on the mattress where the patient is lying. From this pressure map, the system attempts to guess the body parts that cause that pressure and its magnitude. Since the patient may move around in the bed, it can be difficult to ascertain if the pressure at any given area of the mattress is still being caused by the same body part. Using these methods, accurately estimating the impact of pressure on specific body parts has proved to be difficult in practice, involves complex computations and expensive to implement & deploy. There have been several proposals to improve upon this process by use of camera and/or other locationing technologies to augment the determination of patient position, International Patent No. WO2015054423 but they all suffer from additional complexities without adequately solving the inherent issue of measuring the pressure at various body parts accurately. Yet other solutions employ turn indicator to record and report if the patient has been turned. Since the turn indicator is typically mounted in a chest area, it does not measure the pressure at all but more geared towards enforcing the manual turn policies.

The second class of solutions attempt to measure pressure directly at the body parts/limbs by use of patches that contain a pressure sensor. U.S. Pat. No. 6,287,253 describes the use of a transducer based pressure sensor that can be applied to human body. This pressure sensor detects either presence and absence of a preset pressure threshold on the various points of the body which is then read by a nearby transmitter-receiver system using a frequency resonant method. The status of pressure on/off is read periodically via polling and sent it to their controller for reporting purposes. There are several important differences between the systems described in U.S. Pat. No. 6,287,253 and the invention described here which have profound impact on the utility and effectiveness of the overall system.

First, their invention's primary focus is the design of the pressure sensor and enable its reading via a resonant frequency to nearby readers. There are several limitations to their system. Each of their sensors need to be preset to specific pressures on/off thresholds based on the location on the body. This poses an suitability issue as the risk of forming an ulcer is a function of the amount of pressure applied over time. If the amount of pressure exerted is highly approximate (present/not present) then it impacts the ability of the system to assess risks accurately. The resonant frequency technology used for communicating this pressure on/off information may be limited in its range and may pose difficulties when the patient is lying on top of the sensor. Lack of intelligence in the pressure sensor means that the sensing unit may not have software configurable thresholds, may not easily adapt to the needs of different patients, may not support a local decision engine, generate local alarms or support two way communication. The lack of intelligence in the sensor also implies that system configurability is difficult and may have to be supported at the time of manufacturing while scalability of the system is limited as each pressure sensor needs to be tuned to a different frequency along with possible corresponding changes in transmitters & receivers used to read them. The standalone pressure sensor in absence of intelligent architecture is also not extensible as it does not support other sensors in an integrated manner required for improved patient monitoring. Finally, deployability of such a system may be difficult if multiple transmitters/receivers per patient are required.

SUMMARY OF THE INVENTION

The present invention addresses the shortcomings mentioned above and provides a dynamically adaptable, scalable, extensible, easily deployable, closed loop system that incorporates an innovative intelligent sensing unit (ISU). According to an aspect of the invention, the ISU employs a flexible fabric-type pressure sensor. The ISU has a microcontroller, which reads a wide range of pressure values, can perform local decisions, generate local alarms and work in conjunction with an analytics engine to analyze the pressure-time data streams, and continually improve the monitoring process via historical analysis to generate the best possible alerts.

According to another aspect of the invention, the ISU issues warnings or actuates control mechanisms to affect the pressure experienced by the patient body parts, thereby preventing the onset of these pressure ulcers.

According to still another aspect of the invention, the inventive ISU may employ additional medical sensors and devices to alleviate or treat other medical conditions besides pressure ulcers.

This intelligent sensor is suitable for assessing the risks of a pressure ulcer because it can accurately measure pressure over a wide range of values. It is easily configurable because configuration parameters such as sampling rate, averaging window for processing of data, local alarms and some corrective actions can be executed by the intelligent sensor This intelligent sensor helps make the overall system architecture extensible as additional sensors for temperature, humidity, motion and others can be easily integrated, and the information synthesized and sent over to a central server and the analytics engine. This helps in two significant ways. First, these additional measurements can be used to enhance the accuracy of pressure ulcer risk assessment. For example, it is known that a local increase in humidity and/or temperature may accompany a rise in risk of pressure ulcer formation. Second, it can enable the applications that can detect conditions in addition to that of pressure ulcer formation. It can support new applications including but not limited to fall detection and early mobility protocols. Additionally, this intelligent sensor can house modules that can take actions for curative purposes upon receiving commands either from the local decision making software or a remote server.

The overall system capitalizes on the intelligent sensor to deliver a slew of benefits. For instance, the system is dynamically adaptable to patient requirements. It is adaptable because different alert/action thresholds can be set for each patient. This is important because the risk of pressure ulcer formation depends upon the condition of the patient which is higher for geriatric patients. Similarly, babies may have different pressure thresholds than adults. The system is dynamically adaptable because as the patient's condition changes for better or worse the specifications of thresholds and the monitored conditions may be altered accordingly.

Importantly, the present invention is scalable. Thousands of patients can be monitored simultaneously without impinging on the ability of the ISUs, wireless communications networks, or software processing to scale and handle the load. This is because the present invention recognizes upfront that deploying this system in a large healthcare facility poses the challenges that a large number of sensors in close proximity must share wireless space efficiently, must be easily associated to a specific patient, and large scale provisioning and configuration performed seamlessly. The present invention has been carefully designed to be easily deployable by designing controllers that can handle large number of sensing units, single point of system wide configuration through a Graphical user Interface (GUI) that can run on a PC/Tablet or a Smartphone.

Finally, the present invention enables a closed loop feedback system that involves not only the intelligent sensor but also the central server and other actuator devices for corrective actions. For example, in one embodiment of the operation of the system, the alerts may be received by a caregiver or a healthcare practitioner who may then change the position of the patient manually to relieve pressure on the affected parts.

However, in another embodiment of our system, its closed loop control feature can, with the help of the Analytics and control software modules on the server, provide control feedback to an optional automated corrective contraption such as a sectionally inflatable mattress or vibrating mattress described in US Patent No. 2011/0239370 and U.S. Pat. No. 8,011,041. Thus in our system if a prolonged, harmful pressure is detected on a specific body part, instructions may be sent to an inflatable cushion/mattress to relieve the pressure on the affected parts.

Alternatively, the Analytics and Control software modules can issue instructions to the Intelligent Sensor to dispense certain medications using new advances in Microfluids microelectronics (e.g., U.S. Pat. Nos. 6,951,632, 7,470,547 and 7,359,765).

The present invention offers novel, unmatched benefits to help prevent the onset of pressure ulcers—the occurrence of which have been and still are a huge medical burden on patients at home, hospitals and nursing homes worldwide. The current methods of turning every two hours does not take into account the pressure exerted onto the pressure points, nor does it take into account different patient's may require more frequent or less frequent turning. The inventive system can effectively prevent pressure ulcers from occurring or at the onset while potentially minimizing the burden on the caregiver/practitioner.

This invention teaches two significant aspects of innovation: First, it discloses an effective, simple and practical system that uses thin, stick-on wireless sensors (i.e., "smart bandage") to detect pressure on specific parts of the body. The sensing element can be applied onto the patient skin directly or over an existing bandage. It can also be integrated into the clothes, furnishings or bed mattresses. These pressure readings over time are reported wirelessly to a nearby Controller Unit which may further communicate the information to a server which is running analytics software. Once this software recognizes the buildup of pressure on a specific body part it initiates preventive actions to help prevent the onset of ulcers in two primary ways: (1) it generates notifications for the caregiver/medical professional; and (2) it may send control messages to a controllable, inflatable cushion or mattress to take preventive actions and alleviate the pressures.

The second aspect of innovation of the present invention is in devising a closed loop feedback system that can take corrective actions in response to observations from the intelligent sensing units attached to the patient. It demonstrates how the pressure on one part of the body can be reduced by using an innovative search algorithm that overcomes the technical limitations of an open system with no feedback.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings:

FIG. 5 illustrates an Electronically Controllable Recliner;

DETAILED DESCRIPTION OF THE PRESENTLY PREFERRED EMBODIMENTS

Figure 1A:
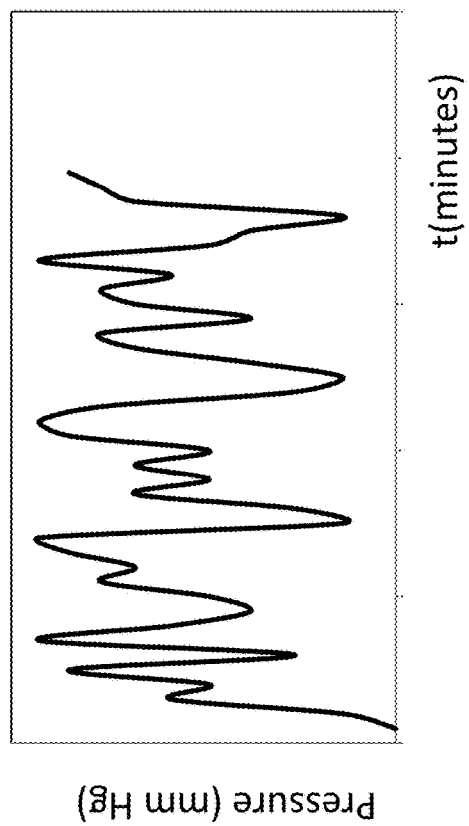
FIG. 1A illustrates the graph of Pressure over Time.
Figure 1B:
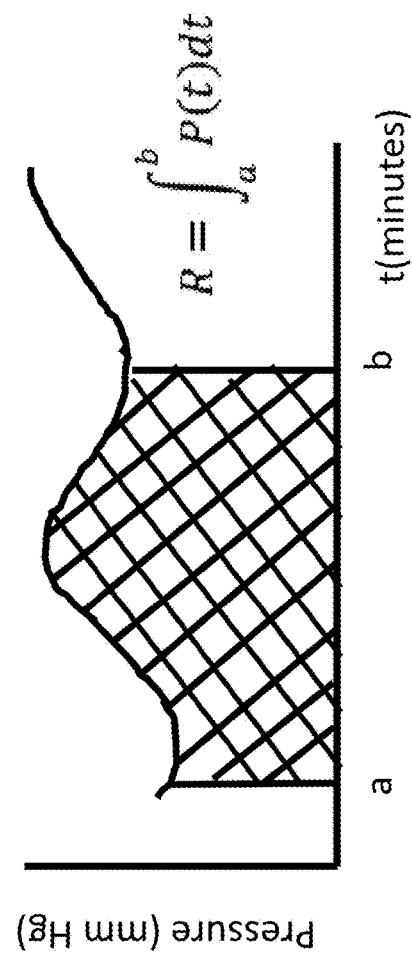
FIG. 1B illustrates the Integration of Pressure over Time.

Pressure Ulcers are formed when a prolonged, sustained pressure is applied at specific patient parts that support the partial or the entire weight of the patient. For any given support point, such as the heel when the legs are resting on a bed, the pressure-time graph may vary with time as shown in FIG. 1A. Typically, the risk is greater if the pressure is greater and/or if it is applied for a longer time. In its most simplistic form this risk can be calculated by integrating the applied pressure over time as shown in FIG. 1B which can be called the simple, integral risk predictor function. However, there are many nonlinear variables e.g. patient weight, current medical condition, prior medical history that need to be captured in the formulation of an ideal pressure ulcer risk predictor function. Yet, all these risk predictors, require an accurate measurement of pressure over time at the specific body part being considered.

The present invention not only provides a method and system for accurate measurement of pressure over time on a specific body part but also includes a framework for predicting the pressure ulcer risk for a given patient, continually improve the system's ability to predict these risks for the monitored patients and last but not least provide a control feedback loop to enable automated corrective actions.

Figure 2:
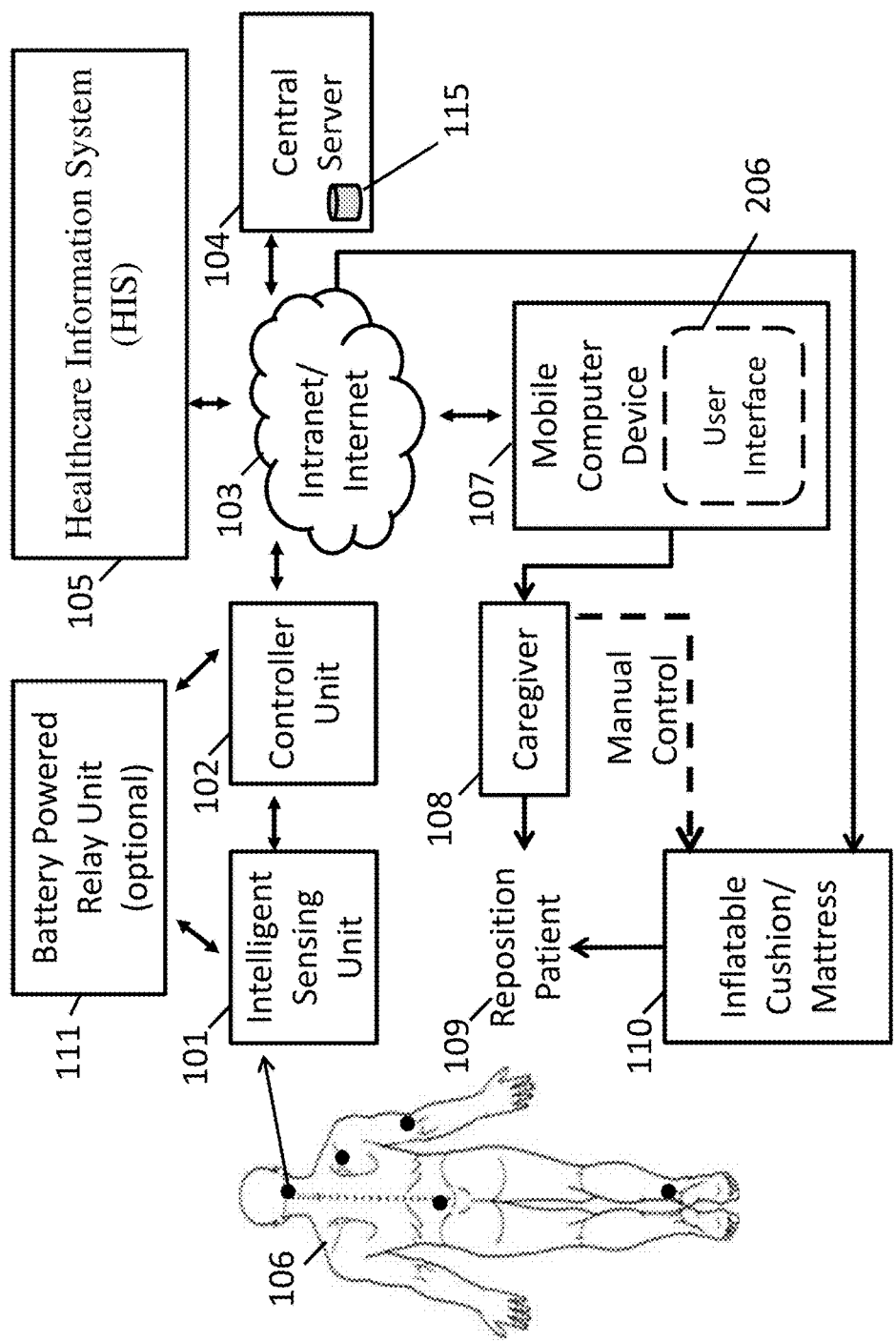
FIG. 2 diagrammatically depicts a preferred embodiment of the inventive system.

FIG. 2 illustrates the presently preferred embodiment of the inventive system and the components required for deployment and use. The various components of the system are the Intelligent Sensing Units (ISU) 101 that are placed on various body parts of the patient 106. One key function of the ISUs 101 is to measure the pressure at the body part to which they are applied and communicate it to the Central Server 104 via the Controller Units (CU) 102. The CUs 102 that communicate with ISU 101 may be assigned either to a single bed, single room covering multiple beds or multiple rooms. Their placement may vary based on the coverage design. An optional Battery Powered Relay Unit (RU) 111 that may be typically mounted on the patient bed is used for ease of associating ISUs 101 with a particular bed in the event that Caregiver 108 does not have access to a User Interface 206 through a Mobile Computer Device 107, such as Smartphone, computer tablet or laptop. The CU 102 communicates with the Central Server(s) 104 that runs the main software components of the system and communicates with the User Interface (UI) 206 available on Smartphone/PC/Tablet using 107, an Intranet or Internet. The Central Server 104 interacts with the Healthcare Information System (HIS) 105 to obtain, at the minimum, information about the patient names and their bed assignments. Database 115 whose implementation may be distributed, is used to store the information which is consumed and produced by various software modules running on the Central Server 104. UI 206 running on Smartphone 107 is used by the Caregiver 108 to specify alert thresholds for patients, and specify actions to be taken when those thresholds are reached. When receiving an alert on Smartphone 107 the Caregiver 108 may reposition patient 109 manually to relieve the pressure. Alternatively, if the Caregiver 108 has specified that the system may take automated corrective actions then the system sends instructions to an inflatable Cushion/Mattress 110 (if available) to relieve the pressure at the affected body parts.

Typical Use of the System

From the practitioner/caregiver 108 perspective, a typical use of the system once deployed is fairly straightforward as follows.

(1) The healthcare practitioner/caregiver 108 first activates all the ISUs 101 that are required to be placed on the patient. At this stage the caregiver 108 also specifies the bed which the patient is using through the UI 206 on Smartphone 107.

(2) The caregiver 108 waits for confirmation that all the ISUs 101 have been associated with the bed and therefore the patient and then applies them onto the patient's 106 body part(s) such as the heel, sacrum, or other parts as required. ISU 101 may be applied on the side of a medical grade bandage away from the patient. When other types of sensors are deployed that require a direct contact with the skin then the unit may be applied directly to the skin.

(3) The medical professional may then optionally set the threshold value using UI 206 or use default thresholds as determined by the Central Server 104.

(4) Once the pressure-time threshold is exceeded on any sensing unit, an alert or notification may be sent to one or more of ISU 101, CU 102 and Smartphone 107.

(5) In addition, if there are electronically controllable inflatable mattress/cushions 110 or drug dispensing capabilities available then the system may take automated corrective actions.

It is important to point out that with this invention, the caregiver 108 may not have to take any further actions beyond steps (1) & (2) for many default patient profiles.

Operation of the System

Figure 3A:
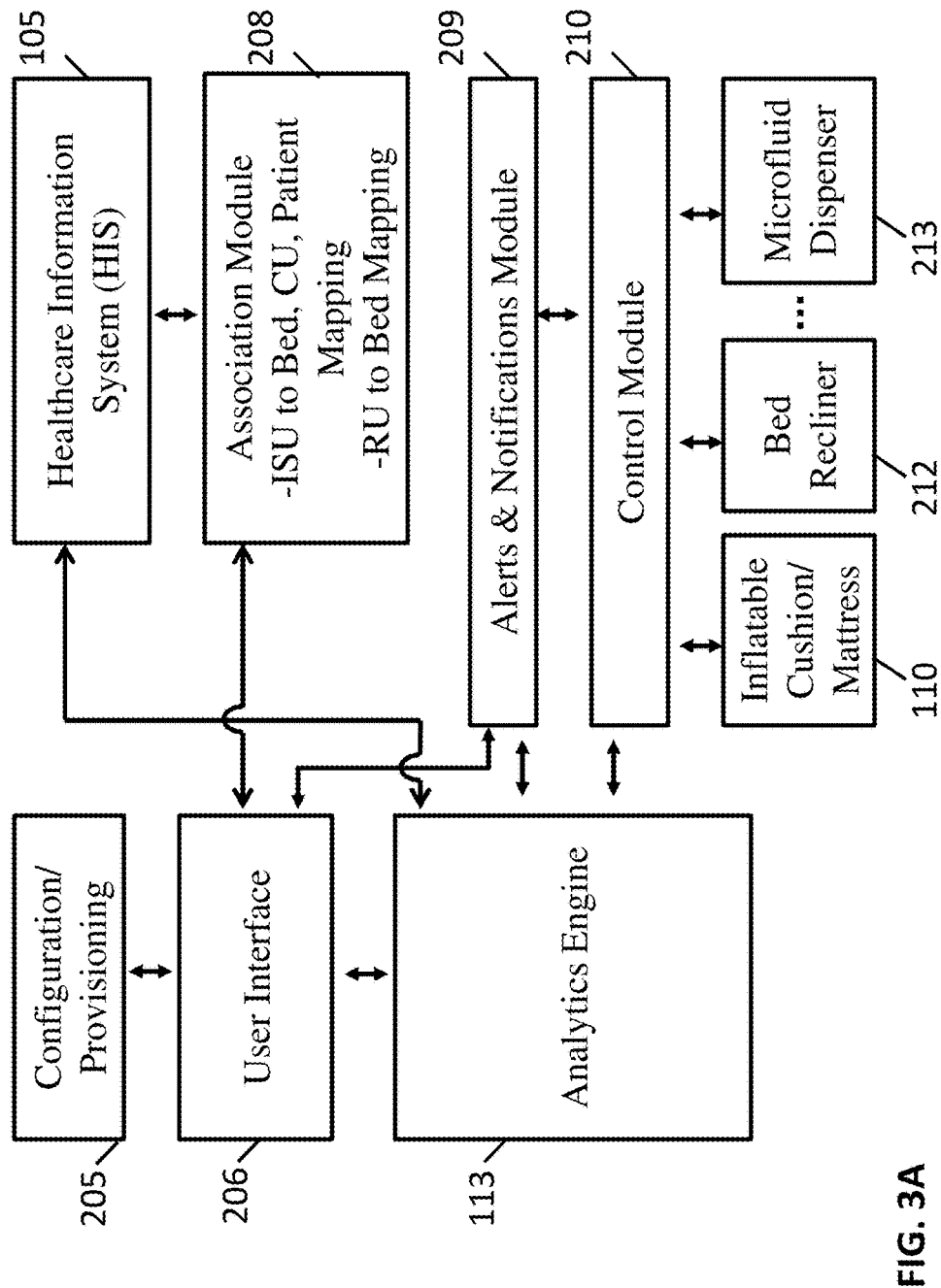
FIG. 3A illustrates a functional diagram of the inventive system.

FIG. 3A depicts the functional block diagram of the inventive system. The functional blocks may approximately correspond to the key software modules of the system with the caveat that some functionalities may be distributed among several modules. The User Interface 206 describes a multitude of user interfaces available across multiple devices and supports both the system administration activities of configuration and provisioning 205 as well as the Caregiver's 108 need to set patient specific parameters and actions in Analytic Engine 113 and Alerts and Notifications Module 209. The Configuration and Provisioning module 205 is responsible for the configuration and management of all network and system elements that constitute the overall system including connectivity, authentication and security settings. The Association Module 208 is responsible for generating and maintaining relationship tables between system elements involved in the care of a patient 106. This includes the ID of the bed assigned to the patient, the ID of the CU 102 that communicates with ISUs 101 attached to the patient on that bed, all the ISUs 101 associated with the patient 106, their functionalities and location on the patient's 106 body. The Alerts and Notifications module 209 is a repository of alert thresholds and actions that have been recommended by the Analytics Engine 113 but which may be superseded by the Caregiver 108 via User Interface module 206. All these modules use databases 115 to store and retrieve information. Many of these modules may be executed on the Central Server 104 though modules such as the User Interface 206 and may necessarily have components that run across multiple devices.

The system receives its inputs from four distinct sources. The first source is from the ISUs 101 that produce a stream of measurement data. The second source is the Caregiver(s) 108 who may specify patient specific parameters such as pressure-time accumulative thresholds and preferred actions and through User Interface Module 206. The third source is the Healthcare Information System (HIS) 105 that among other information provides patient condition, history and bed information to Association Module 208. The fourth source is Configuration and Provisioning module 205 that takes input from System Administrators required for seamless operation of the system including number and placement of CUs 102, network IDs, passwords, and User Administration.

The system produces two kinds of output. The first is a set of alerts and recommended action notifications for the Caregiver 108. This output may also be shared with Health Care Information System (HIS) 105. The second kind of outputs is via the control modules 210 that are capable of issuing corrective commands or actions to Inflatable Cushion/Mattress 110, Bed Recliners 212 or Microfluid Drug Dispensers 213. The module that is responsible for analyzing data, determining alerts, updating models, and undertake corrective actions is the Analytics Engine 113 which is described later.

Description of the Feedback and Control Loop

Figure 3B:
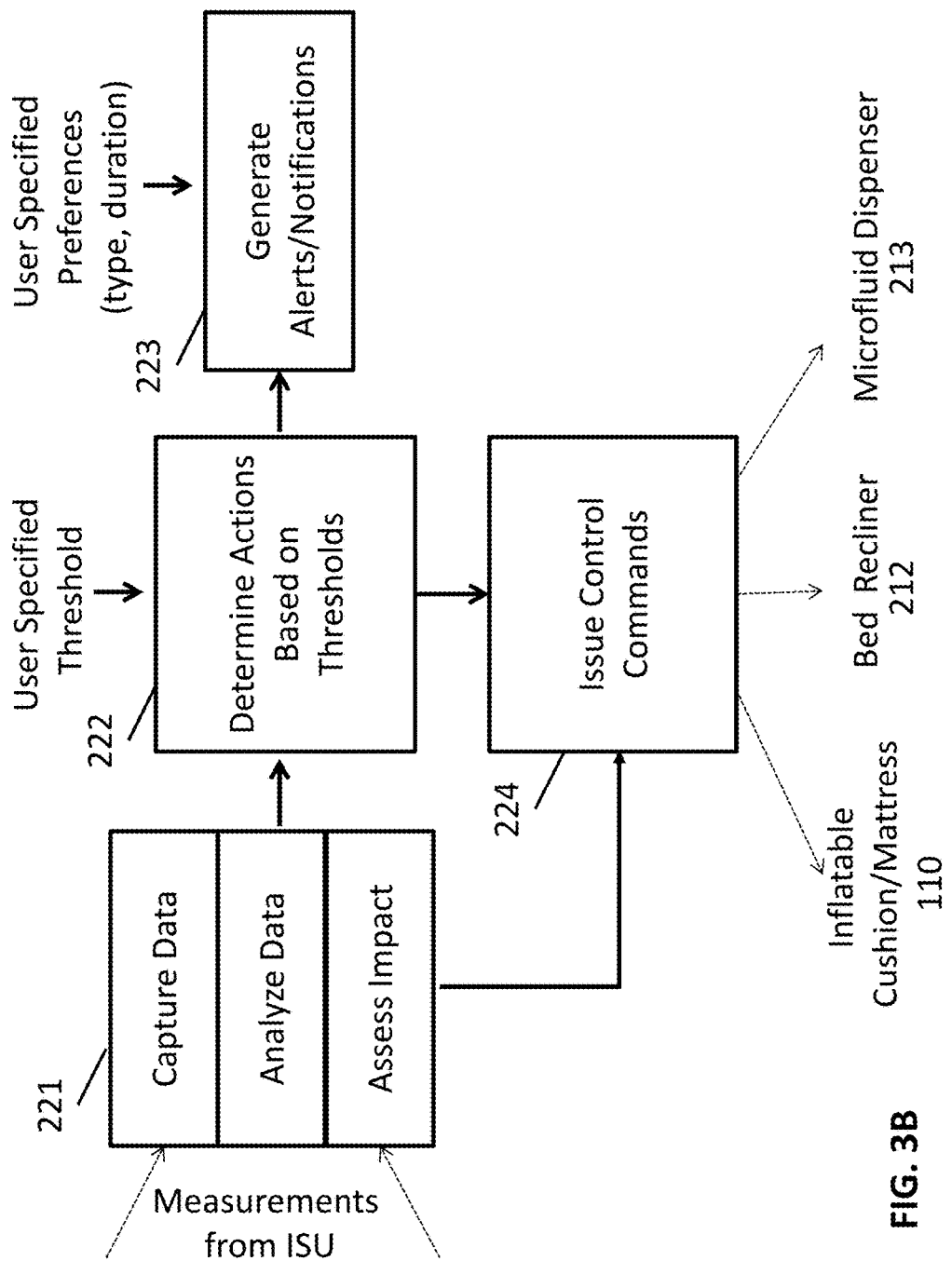
FIG. 3B illustrates the control loop with feedback in the inventive system.
Figure 4C:
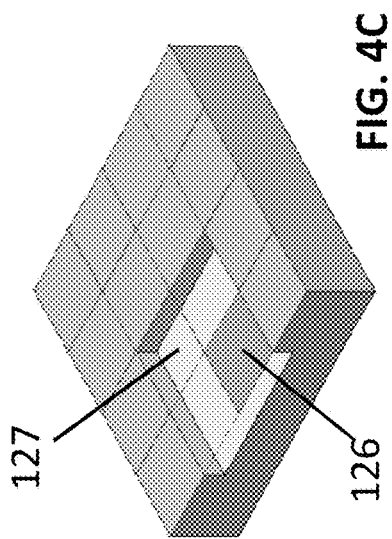
FIG. 4C illustrates the new grouping for the second phase of search.
Figure 4D:
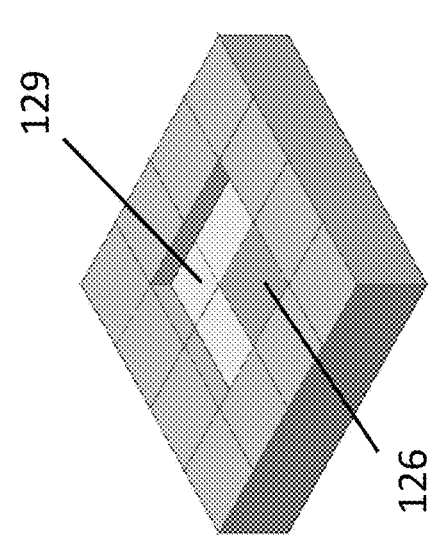
FIG. 4D illustrates the alternate grouping for the second phase of search.
Figure 4A:
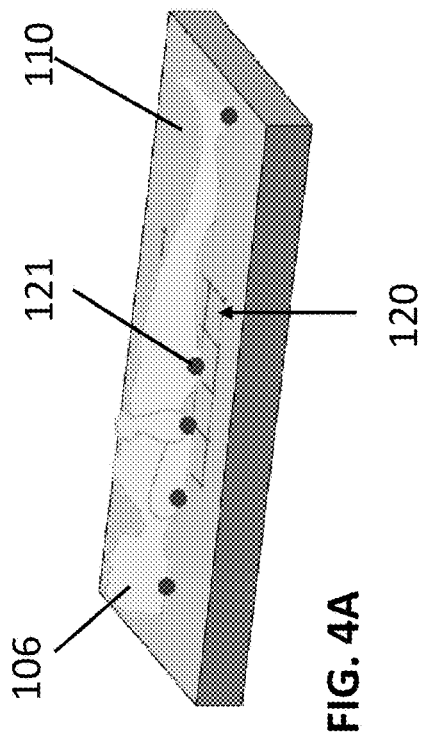
FIG. 4A Illustrates the Support points of inflatable mattress.
Figure 4B:
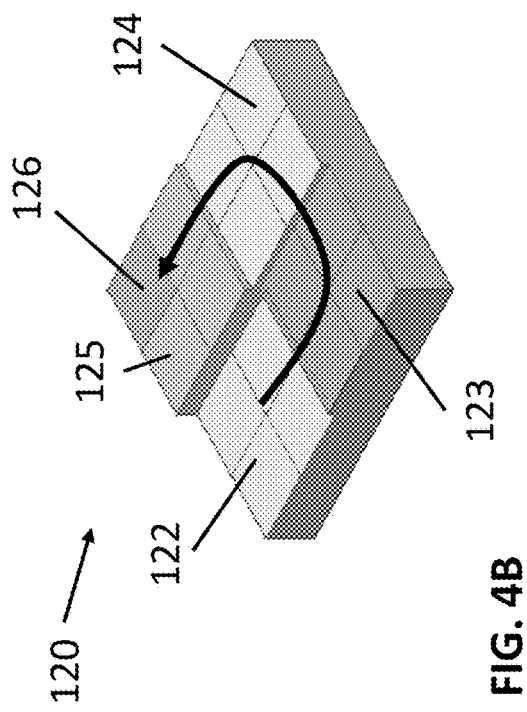
FIG. 4B illustrates the Initial grouping for the first phase of search.

The feedback and control loop as illustrated in FIG. 3B works functionally as follows. The functions described in FIG. 3B are implemented by modules described in FIG. 3A on the Central Server 104. For each patient 106, the Association module 208 maintains a table of all the ISUs 101 attached to a patient 106 and their precise location on the patient's body using database 115. As the ISUs 101 send their measurements to the Central Server 104 via the CU 102, the Central Server 104 continually analyzes the measurement stream to determine if the cumulative duration & magnitude of pressure reported by ISU 101, mapped to a specific body part of the patient 106 has exceeded specified thresholds. This is depicted as a functionality in 221. Function block 222 determines what actions needs to be taken based on thresholds that may be specified by the Caregiver 108. If so, then the function block 223 denotes the generation of an alert that is sent to Caregiver 108 via a mobile device such as a Smartphone, a laptop, a PC, or a computer tablet 107. In addition, the Central Server 104 may issue control commands using Control Module 210 to a controllable, Inflatable Cushion/Mattress 110 or Incliner to take corrective actions. The inflatable Cushion/Mattress 110, is equipped with pumps that can individually control the inflation and deflation of the various sections of the Cushion/Mattress 110. The Bed Recliner incliner 212 is equipped with controllable motors that can change the inclination of the various sections of the bed. As shown in FIGS. 4A, 4B, 4C, and 4D, 120 denotes the support points that carry the weight of the patient. FIG. 4A shows exemplary support point 121 that is in contact with the mattress 110. By selectively inflating or deflating sections of the mattress 110 or changing the incline angle of an appropriate portion of the Incliner, pressure on the support points, a pressure at specific body parts may be alleviated.

FIG. 4 also shows that an inflatable mattress 110 may be divided into sections (e.g., rectangular) that are referred to as compartments 126 each of which may be individually inflated or deflated. For our purposes it is desirable to have compartments 127 which are no bigger than 4"×4" for an adult and maybe as little as 1"×1" for a baby. To illustrate the working of our closed loop system, it may be helpful to consider an ISU 101 that was applied to the sacrum area 121 of patient 106 and whose pressure-time measurements were flagged by the Central Server 104 to indicate that the acceptable thresholds have been breached or exceeded. The Central Server 104 now needs to send instructions to the compartments 126 supporting the sacrum area 121 of the patient for deflation or inflation to relieve the pressure on the sacrum. However, before it can do that it needs to know the position of the patient on the bed/mattress and in particular it needs to determine the location where the sacrum is situated so that pressure in the right compartments can be changed. Therefore, the control algorithm has two steps. The first step determines the position of the sacrum 121 as it relates to the bed/mattress. The second step involves inflating and deflating the compartments to an appropriate pressure so that the pressure on the sacrum is alleviated. $P_1$ denotes the pressure magnitude steps that will be used to deflate or inflate compartments to determine the position of sacrum at it relates to the inflatable bed/mattress. Typically $P_1$ should be small enough so as not to noticeably impact the patient but at the same time large enough to be observable by ISU 101. $P_t$ is the target desirable pressure for the sacrum. $P_c$ is the pressure increments by which the compartments 126 may be inflated or deflated in order to reduce the pressure on the sacrum to $P_t$.

The steps are described in details below.

Step 1: (Determining the Position of the Sacrum on the Bed/Mattress)

Given the identification of the ISU 101 and the knowledge that this ISU 101 was applied to the patient's sacrum area 121 an initial area of several compartments 120 is estimated. For example, FIG. 4B denotes the 16 compartments on which the sacrum may be situated. The algorithm for finding the compartment(s) where the sacrum is currently situated is as follows. The 16 compartments are divided into 4 adjacent groups 122, 123, 124, and 125 of 4 compartments each. Each group is deflated sequentially in steps of $P_1$ and the corresponding pressure change on the ISU 101 is observed. There are basically four possibilities that emerge out of this as the ISU 101 may observe a lower pressure by deflating either 1, 2, 3, or 4 groups of compartments. If there are two groups 122, 123 that cause the drop in pressure observed by the ISU 101 then it is possible that the sacrum area overlaps the two groups. A new group G of four compartments 127 is formed as shown in FIG. 4C. If 3 or 4 groups cause a change in pressure then a new group G of four compartments 129 is formed as shown in FIG. 4D.

Now we have a group of 4 compartments arranged in a square on which the sacrum may be situated. Each of these compartments 126 is now deflated in turn thereby determining which compartment(s) result in reduction in pressure on the ISU 101. The group of compartments $C_g$ that causes the change in pressure in ISU have now been identified to impact or affect the pressure on the ISU 101.

There are a number of refinements to the algorithm that can leverage varying search strategies, exploit the observed changes in pressure magnitudes but at the core this algorithm is highly efficient in that it requires only three phases of deflation-observation cycles to identify the compartments that impact the pressure on the sacrum in this particular example.

Step 2: (Modifying Pressure on Patient Body Parts)

Once the compartments $C_g$ that impact pressure reading of ISU 101 on the sacrum 121 have been identified, then the compartments 126 are deflated in increments of $P_c$ until the desired pressure $P_t$ is observed at and reported by ISU 101. It is also apparent that in some cases, if the compartments are much bigger than 4"×4" as desired then the system may reduce the pressure in one large compartment in the general location of the sacrum.

There are alternative devices such as bed recliners 150 that may also be used to relieve the pressure. The recliners typically provide the ability to raise the upper or lower parts of the body as shown in FIG. 5 and change the pressure vector (e.g., along and perpendicular to the support surface) and thus the magnitude of pressure on the support points thereby reducing pressure on upper or lower parts correspondingly. Here, pressure on the sacrum and upper parts of the body can be relieved by raising the upper part of the bed while pressure on lower extremities of the body such as buttocks, heels can be reduced by raising the lower portion of the bed. The algorithm for relieving the pressure on the sacrum is as follows. The upper part of the bed is inclined upwards stepwise in angle increments of $A_c$ until the desired reduction in Pressure on the ISU is lowered to $P_c$.

In yet another embodiment, if the ISU 101 is equipped with drug dispensing capabilities then instructions may be provided by the Central Server 104 to ISU 101 to dispense a specific drug.

Intelligent Sensing Units (ISU)

Figure 6:
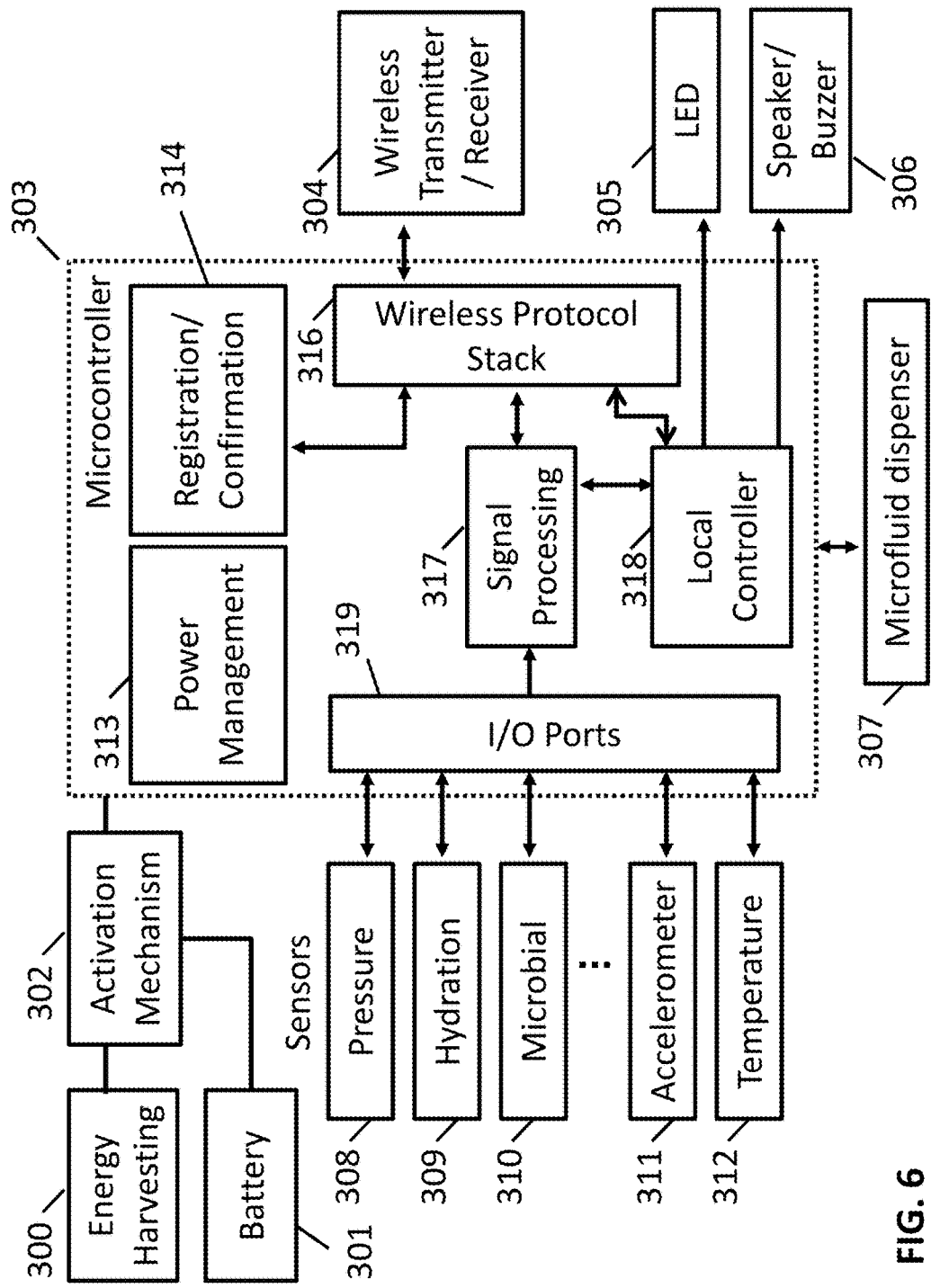
FIG. 6 illustrates the block diagram of the Intelligent Sensing Unit (ISU)

FIG. 6 illustrates a functional block diagram of the Intelligent Sensing Unit (ISU) 101. Microcontroller 303 is the heart of the ISU 101 that interfaces with the sensors, executes all the software modules on the ISU 101, controls the local notification devices and manages the wireless communication with the CU 102. From a hardware perspective, the microcontroller 303 consists of a CPU, memory, and I/O ports 319 for sensor communication, controlling serial devices, and data communication. When configured for the prevention of pressure ulcers, the ISU 101 is equipped with a pressure sensor 308. Optionally, the ISU 101 can be equipped with additional sensors for temperature 312, hydration 309 or microbial 310 all of which are not only indicators of pressure ulcer risk but can also be used in the detection and management of other medical conditions. The accelerometer 311 can be used to detect mobility that not only helps with the determination of position but also helps in determining the extent of patient movement that is indicative of the patient healing process. Each sensor may be assigned to a separate I/O port but if the number of sensors exceeds the number of I/O ports on the microcontroller 303 then the sensors are multiplexed into the Signal Processing module 317 of the Microcontroller 303 using a timing signal generated by the microcontroller central processing unit (CPU). This timing signal, generated by the CPU, selects the sensor from which data stream is being read. Since this timing is controlled by the CPU then it becomes feasible for all the software modules running on the CPU to know the sensor from which the data is being collected. The CPU typically runs at much higher speeds than the rate at which data is being produced by all the sensors thus insuring that no data is ever missed due to multiplexing.

The Signal Processing module 317 receives the data on which it performs signal processing functions such as sampling, averaging, filtering and other transformations as instructed by the Local Controller 318. The Signal Processing Module 317 then packetizes the data and inserts the originating sensor information into the packet before handing it off to the Wireless Protocol Stack 316.

The wireless protocol stack 316 is responsible for authentication and implementing a two way secure & reliable communication using the Wireless Transmitter/Receiver 304 which is responsible for RF modulation and demodulation of signals received or transmitted over its antenna. An exemplary frequency band that is used here is the relatively new frequencies mandated in the FCC's Medradio band that specifies that medical devices should be operating within the frequencies of 401-402 and 405-406 MHz for body-worn devices. This is to prevent interference with wireless medical implants, such as wireless pacemakers which operate in the 402-405 MHz range. Although FCC also permits the use of some other higher frequencies for body-worn devices, such higher frequencies are more easily blocked by the human body and may not be able to meet the range requirement of ISU 101.

Local Controller 318 communicates with the Central Server 104 to download patient specific commands that can be used to generate local alerts and any special instructions for the Signal Processing module 317 that specify parameters such as frequency of sampling, or windows size for averaging. The microcontroller 303 also has a software module for Registration/Confirmation 314 that implements the protocols for registering the ISU 101 with the Central Server 104 when first activated and then recording the confirmation that it has been registered.

Since the energy efficiency of the ISU 101 is paramount, the microcontroller has a very important Power Management module 313. This power management module 313 interacts not only with each of the other modules in the microcontroller 303 to optimize their energy consumption impact but also with the entire microcontroller 303. Thus the power management 313 module can put the microcontroller 303 and, through the I/O control port, put the wireless transmitter/receiver (or transceiver) 304 in a low power state and then wake it up (i.e. in a higher power state) only when it needs to capture and transmit sensor data. Once these tasks are complete it can then revert the ISU 101 into a low power state where the quiescent current is a fraction of the normal current when the ISU 101 in its fully awake state. The time intervals for the sleep/awake state are determined by the Local Controller 318 and are dependent upon the sampling frequency received from the Central Server 104. Another technique implemented by Power Management module saves power by implementing algorithms that transmit sensor values only when they differ from previous ones (i.e. similar to bit coding schemes used to save bandwidth in telecommunication though here they are implemented at higher layers of abstraction).

The ISU 101 can optionally be equipped with a localized notification system, which may be audible and/or visual, such as speaker/buzzer 305 and/or LED indicator 306 that are used to alert Caregiver 105 that a preventive action needs to be taken. The local controller 318 is designed to work with the Analytics Engine 113 and can download and store threshold settings that can be used to generate local notifications and improve response times. This may also be useful when intranet connectivity is lost for some reason. The optional microfluid dispenser 307 can be used to dispense medications directly to the body part for healing purposes. Here the medication dispensation settings, dosage and time intervals, may be downloaded to the local controller 318 from the Analytics Engine 113.

The ISU 101 is designed to be highly energy efficient through hardware engineering and intelligent power management and thus drains little power while in use. Therefore, ISU 101 may be powered by a small ultra-thin and flexible battery 301 and/or through energy harvesting technology 300. The ultra-thin flexible battery is constructed from materials such as alkaline or lithium and maybe as thin as paper (see, e.g., U.S. Pat. No. 8,431,264B2) but have much lower energy capacity. Energy harvesting 300 gathers the ambient energies in the environment and converts it in to electrical energy. Exemplary types of energy harvesting technologies that may be suitable for use in the context of ISU 101 are piezoelectric for capturing the energy of motion (e.g., US Patent No. 20050057123A1), thermoelectric for capturing the energy from the human body (e.g., U.S. Pat. No. 7,397,169B2) or electromagnetic for capturing the energy of radio frequencies (e.g., US Patent No. 20120086285A1).

To increase the shelf life of ISU 101 while in storage, ISU 101 contains an Activation Mechanism 302 that allows the ISU 101 to be powered only when it is desired to be used with a patient 106. The activation mechanism 302 of the ISU 101 involves the use of a tab which when removed closes a circuit and connects the power source, battery 301 and/or energy harvesting technology 300, to all the components in rest of the circuitry in ISU 101. This activation mechanism is described in the next section.

Intelligent Sensing Unit—Assembly, Packaging & Identification

FIGS. 7A, 7B, 8A, and 8B illustrate an exemplary assembly, packaging and identification of the ISU 101. Here, the term "assembly" refers to the assembly of the electronic substrate that houses the electronic components, sensors and battery. The term "packaging" refers to the encapsulation of the assembly in a protective outer-covering that also facilitates how the ISU 101 may be attached to the patient 106. "Identification" is a visible and/or electronic record of the ISU's ID that is typically put on the packaging but may also be etched on to the assembly board.

Figure 7A:
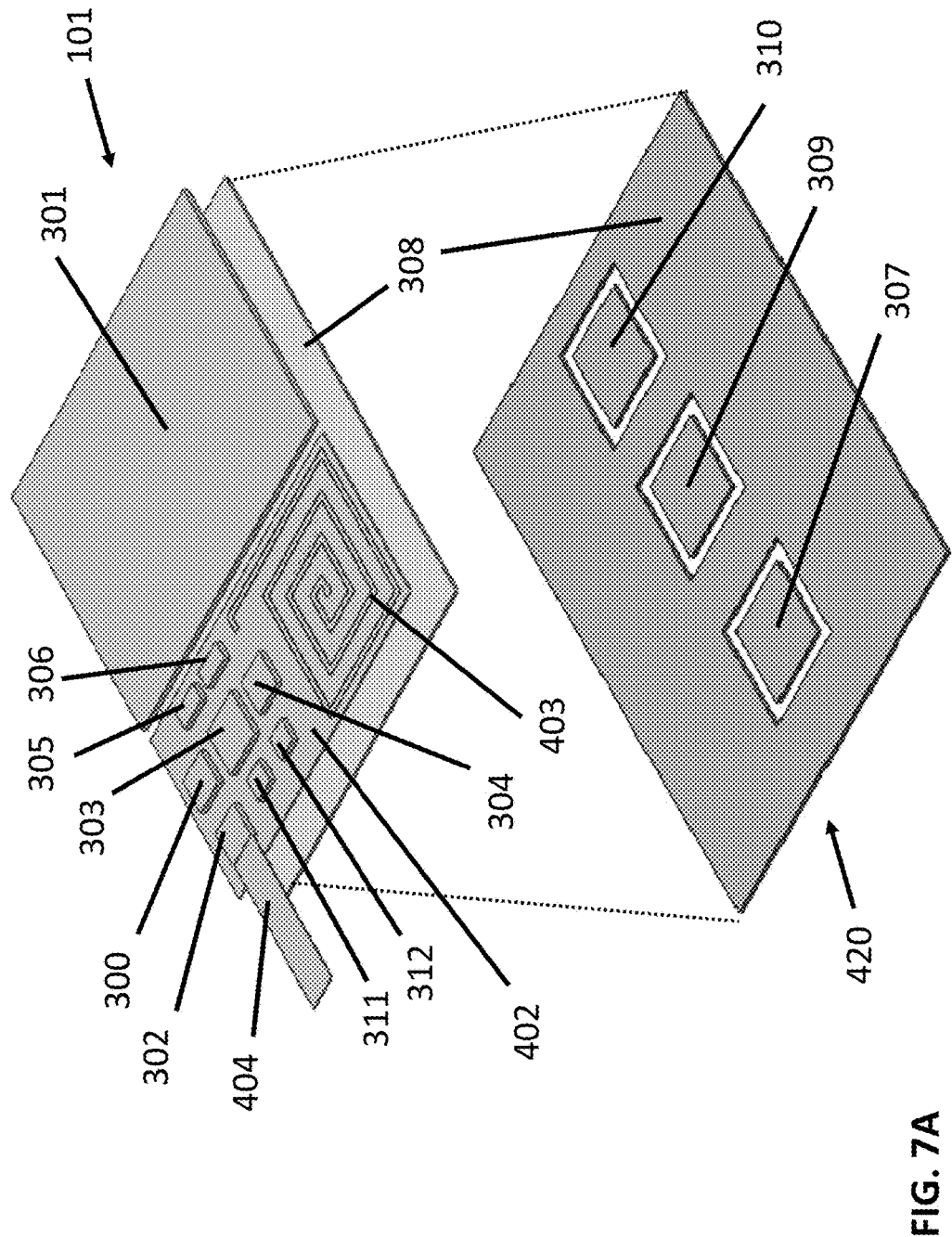
FIG. 7A illustrates the 3D View of the ISU.

FIG. 7A illustrates the three-dimensional (3D) view of ISU 101 assembly for an exemplary pressure ulcer prevention application. The assembly is designed to meet the challenging requirements of ISU 101 which needs to be flexible enough to conform to the shape of the body part and thin enough not to cause discomfort to the patient 106. Here all the electronic components are mounted on the flexible Printed Circuit Board (PCB) 402. Kapton developed by DuPont may be used as the material for fabricating the flexible PCB 402, due to its good electrical properties and being ultra-thin. The thickness of the fabricated flexible PCB depends on the number of layers for wiring and in a presently preferred embodiment, can be as thin as 0.1 mm.

The design of the flexible PCB 402 is done by the use a CAD software tool to layout the traces and placement of all the electronic components using all the available layers in the PCB 402. The electronic components' placement and how they are connected together is critical in fabricating, assembling and packaging the ISU 101 to its final form-factor.

The antenna 403 is designed into the flexible PCB 402 and is situated to the right side of the flexible PCB 402 and away from the electronic components to minimize electrical interference with RF signals. The wireless transmitter/receiver 304 component is placed near the antenna 403 so that it can be easily connected and noise is minimized.

Since the Microcontroller 303 interfaces with all the other components on the board except for the antenna, the Microcontroller 303 is placed at the central position of the flexible PCB 402. This placement allows the Microcontroller 303 to easily connect to all the other components on the board and minimize the overall size of the flexible PCB 402.

The activation mechanism 302 is placed on the left side near the edge of the flexible PCB 402 so that the tab 404 extending out can be easily removed when activating the ISU. When the tab 404 is pulled, the switch in the activation mechanism 302 closes the connection between the battery 301 and the rest of the circuitry. If optional energy harvesting 300 is used, this component is placed close to the activation mechanism 302.

The accelerometer 311 and temperature 312 sensors are placed at the south side of the Microcontroller 303 on the flexible PCB 402 as they do not necessarily need to be in contact with patient skin. The optional local notification system components such as LED 305 or speaker/buzzer 306 are placed at the north side of the MCU 303 on the flexible PCB 402.

The ultra-thin battery 301 is placed to the north side of the flexible PCB. The ultra-thin battery 301 is connected to the flexible PCB 402 using electronically adhesive tape.

The pressure sensor 308 is connected at the bottom of the flexible PCB 402 through very thin flexible wires. The exemplary pressure sensor 308 is made out of a specially coated textile material that changes its resistance under strain from a force. The pressure sensor 308 may or may not need to be in direct contact with the skin but is configured to indicate the strain imparted to the skin of the patient.

There are multiple designs for the pressure sensor. In one embodiment, the pressure sensor comprises three layers that are sandwiched together. The top layer is the anode, the middle layer is the pressure sensing material and the bottom layer is the cathode. The anode and cathode are made from the same material and is usually made of thin sheets of electrically conductive metal, such as copper or gold. Other suitable forms of the anode and cathode include the use of copper textiles. Copper textile may be constructed by blending copper with cotton and woolen fabrics to form a cloth. This makes the copper textile both thin and flexible, and provides an added benefit of comfort. The middle layer for sensing pressure may be constructed from thin sheets of carbon nanotube. Carbon nanotubes have been found to offer excellent electrical and thermal properties that make it suitable as a material for pressure sensing. The carbon nanotubes may be blended with a polymer composite to form a paper-thin sheet that gives it unique properties, whereby the electrical resistance changes with a change in strain.

Another type of pressure sensor may be fabricated from Microelectromechanical System (MEMS), which offers good electrical and mechanism properties and the fabrication is similar to integrated circuits for computer chips, where multiple layers of conductive/nonconductive materials are deposited or etched onto the silicon substrate. The MEMS pressure sensor is constructed by first etching a cavity into a piezoresistive material to form a thin diaphragm, which deflects under pressure. The piezoresistive material is then inverted and bonded to the silicon substrate. When pressure is applied to the diaphragm, the electrical resistance of the piezoresistive material changes correspondingly. The thickness of the MEMS pressure sensor is typically in the range of micrometers.

Accordingly, the total thickness of the assembled ISU 101 is ultra-thin and is designed to fall within a range of about 0.5 mm to 1.0 mm.

If additional sensors 420 are equipped onto the ISU 101 and requires direct contact with the skin, then the pressure sensor 308 may be modified. In one embodiment, the pressure sensor 308 has holes cut out for the placement of the hydration sensor 309, microbial sensor 310, and/or microfluid dispenser 310 as shown on FIG. 7B. The pressure sensor 308, hydration sensor 309, microbial sensor 310 and/or microfluid dispenser 307 are then connected to the flexible PCB 402 shown in FIG. 7B.

Figure 7B:
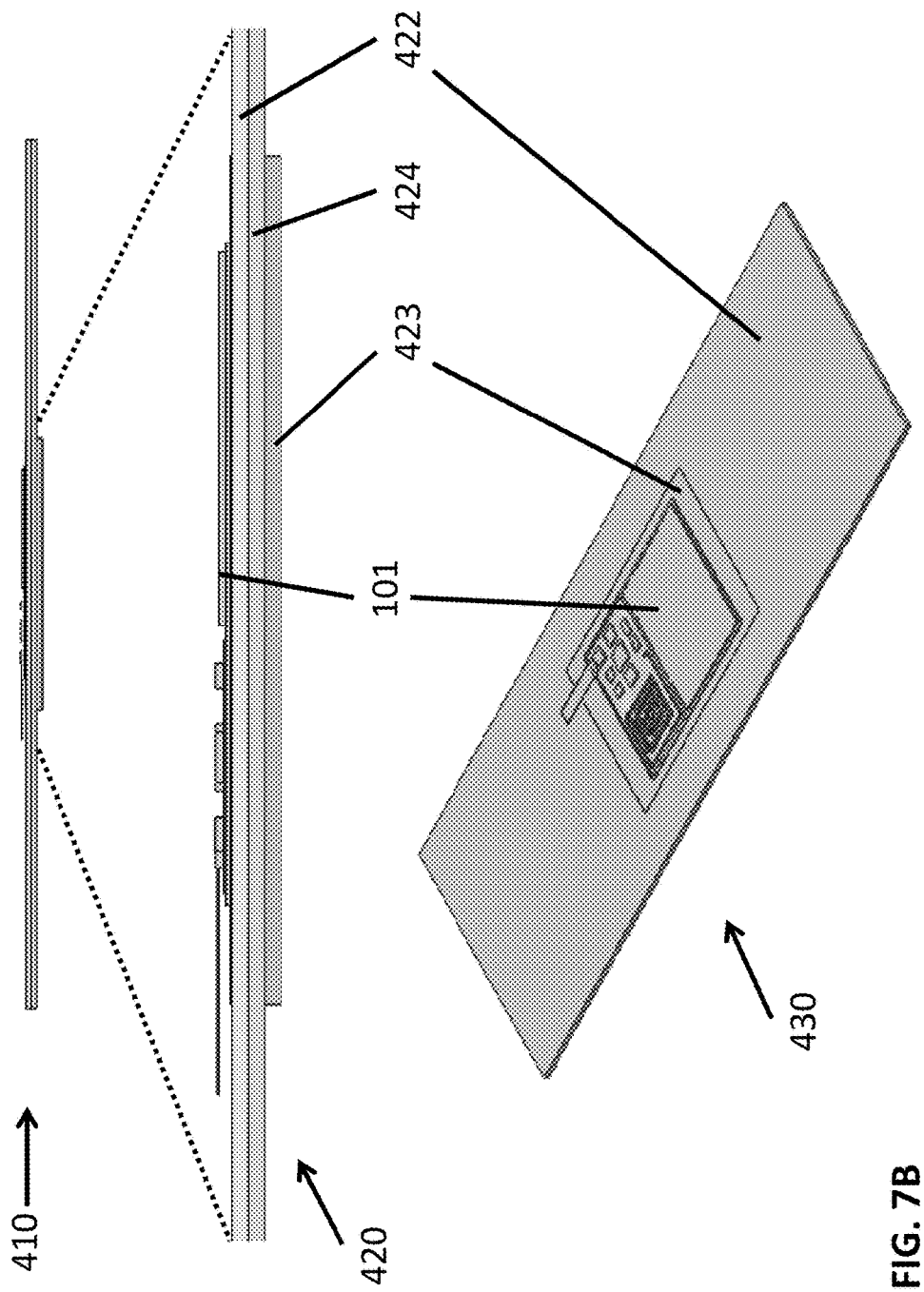
FIG. 7B illustrates the views of the Intelligent Sensing Unit packaging.

After bringing all the components together and assembling it, as shown on FIG. 7A, packaging is needed. FIG. 7B illustrates an example packaging of the ISU 101 bandage. The cross-sectional view 410 of the packaging with a close up view 420 shows the different layers that will be required to package the ISU into a bandage. The assembled ISU 101 is sandwiched into the substrate 422, which may be constructed of medical grade plastic, cloth fabric or thin film, such as, for example 3M™ Medipore™ H Soft Cloth Tape or 3M™ Cavilon™ No Sting Barrier Film. The substrate is then coated with a medical grade adhesive 424, so that it can easy be applied and adhere to the skin of the human body, hospital bed, wheelchair or any surfaces. An optional gel layer 423 can be added to provide cushioning. The 3D view 430 shows the assembled ISU 101 is placed at the center of the bandage and above the optional gel layer 423.

Figure 8A:
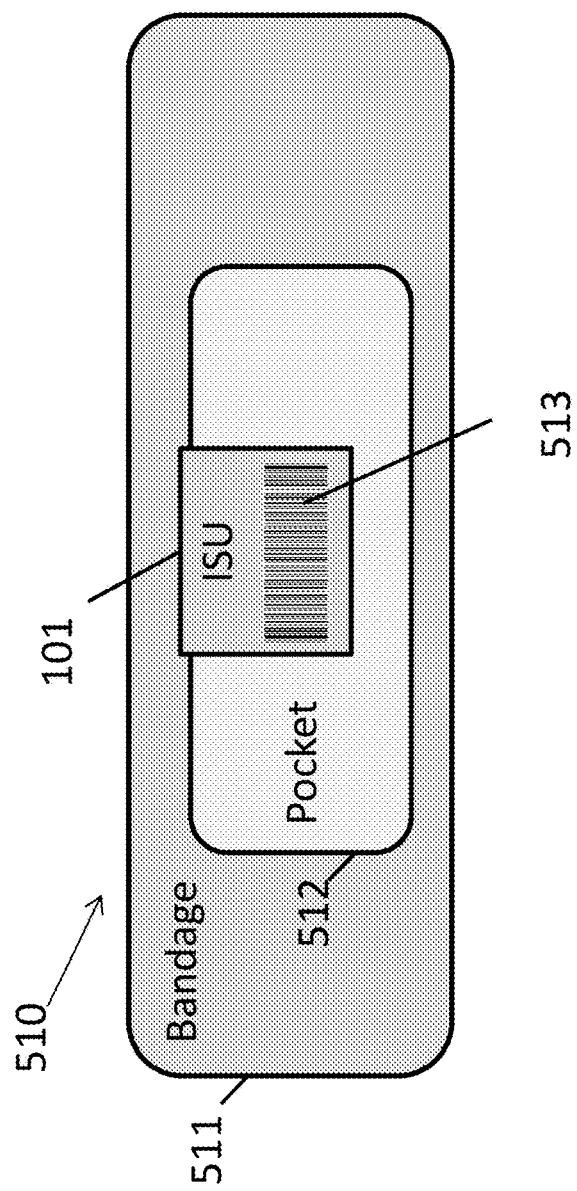
FIG. 8A illustrates an exemplary ISU packaging.

FIG. 8A illustrates another example packaging 510 for the ISU 101 where ISU 101 is mounted on the side of a commercial bandage that is spaced away from the patient. Here, a pocket 512 is added to a suitable commercial bandage 511 so that the ISU 101 can be inserted. This packaging methodology offers the advantage of leveraging existing commercial bandages and thereby simplifying the packaging shown in FIG. 7B. Furthermore, a medical sleeve could be used to prevent the ISU 101 from being soiled.

Figure 8B:
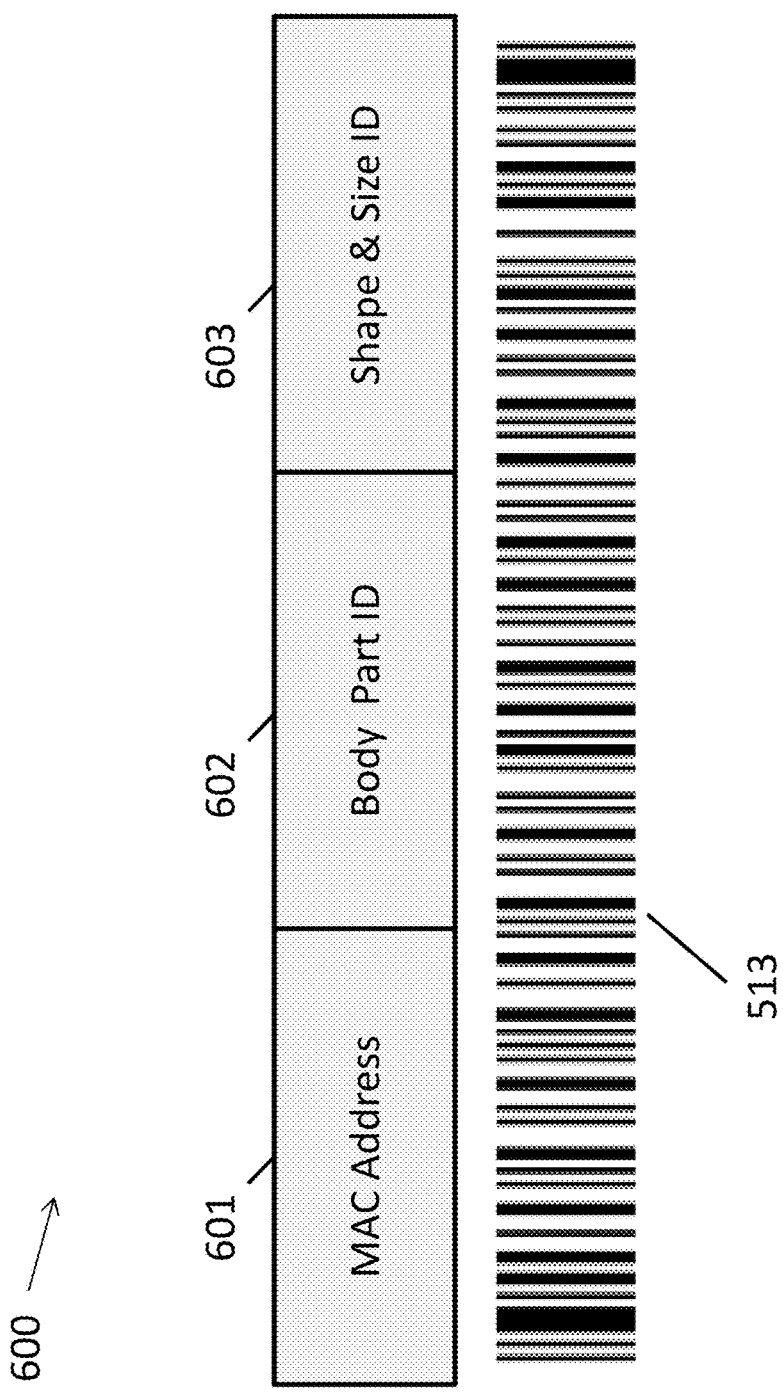
FIG. 8B depicts an exemplary ISU Identification Code schema (i.e. a barcode) printed onto a label on the ISU as a barcode.

FIG. 8B depicts the ISU 101 Identification Code 600 schema (e.g. a barcode 513) that is printed onto the label of the smart bandage 410. The identification code is used for inventory control, management, and association of the ISU 101 to a patient 106 and his body part. The identification code may, at a minimum, include the combination of MAC address 601, body part ID 602 and shape & size identification (ID) 603 to create a unique physical and electronic identification for the ISU 101. The barcode 513 also encodes this information. The body part ID 602 maps the part of the patient body the ISU 101 is attached. The shape & size code 603 can be used to denote the different shapes and sizes of the ISU bandage (e.g., for an adult or adolescent, or for tailbone or a heel). The shape & size code 603 can be used by the feedback system to control the size of the area of a control surface such as an inflatable mattress 110 or reclinable bed 150 to relieve the pressure on a specific body part. Optionally, the ISU 101 packaging may also include a passive radio-frequency identification (RFID) or Near Field Communications (NFC) pattern printed on its outer packaging.

Controller Unit (CU)

Figure 9:
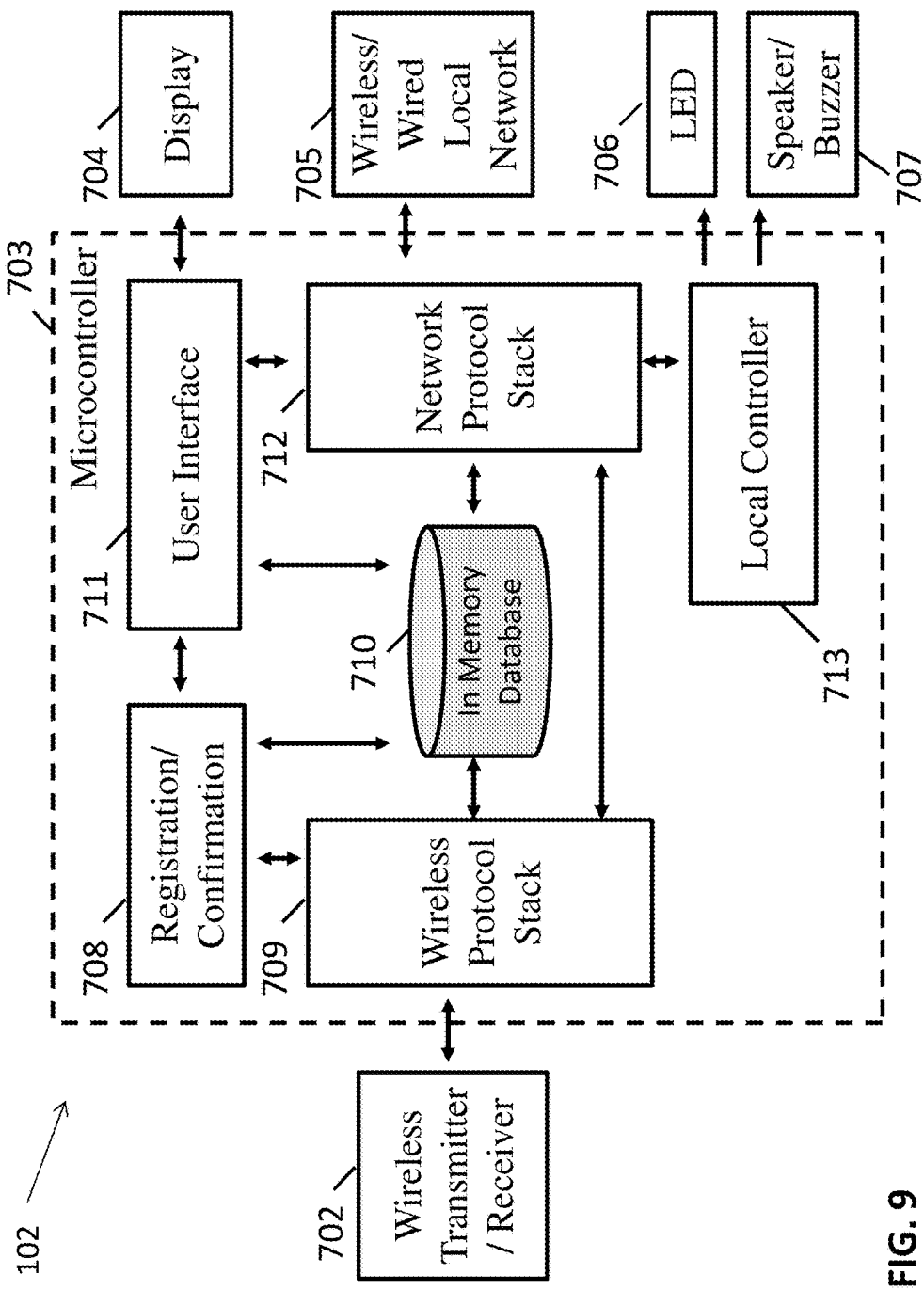
FIG. 9 illustrates the block diagram of the Controller Unit (CU)

FIG. 9 diagrammatically illustrates the Controller Unit (CU) 102 and its various components. CU 102, which may be powered through an outlet on the wall or the bed, performs a variety of key functions in the system. Its key hardware components include (i) the Microcontroller 703 which executes the Registration/Confirmation module 708, wireless protocol stack module 709, In-memory Database (residing in EERPOM) 710, User Interface 711, Network Protocol Layer 712, Local Controller 713, and which controls and communicates through its various I/O ports with a wireless transceiver 702 and a wireless/wired interface 705 with the local area network, (ii) audio/visual devices 706, 707 and (iii) a display 704.

The CU 102 has four basic functions.

(1) First and foremost because the ISU 101 operates on a different frequency in the exemplary band of 405 MHz while the healthcare facility's Intranet 103 may be operating on the Wi-Fi frequency band of 2.4 Ghz/5 Ghz, operating a different set of networking protocols, CU 102 performs a communication bridging function between the ISU 101 and the healthcare facility's Intranet 103. The wireless protocol stack 709 receives all communications data from ISU 101 using the Wireless Transmitter/Receiver module 702. In its simplest embodiment, it may simply forward that data to the Central Server 104 via the Wireless/Wired Local Network module 705. Conversely, it may receive control messages meant for ISU 101 from the Central Server 104 through the Wireless/Wired Local Network module 705 & Network Protocol Stack 712 and forward them to the ISU 101 using the Wireless Transmitter/Receiver module 702 & Wireless Protocol Stack 709. In order to accomplish this function, CU's In-Memory Database 710 (e.g., in EEPROM) preferably includes a table of IDs of all ISUs 101 that have registered with it and also communicate this information to the Central Server 104 so that the Central Server knows that in order to send a message to a particular ISU 101 it must send that message to this particular CU 102. This Registration/Confirmation process executed by module 708 is as follows. When an ISU 101 is first activated it beacons/broadcasts its ID with a special flag which indicates to a listener that it is a request for Registration and then listens for a confirmation response from any CU 102. This cycle is repeated until the ISU receives confirmation from a CU 102. Due to the asynchronous nature of Registration requests, CUs 102 are programmed to listen for these types of broadcasts from ISU 101 periodically. Once a CU 102 receives a Registration request it forwards that request to the Central Server 104. The Central Server 104 typically confirms the first request for registration that it receives and sends a confirmation to the CU 102 that forwarded the registration request while denying other requests it might receive from any other CUs 102. CU 102 sends a confirmation message back to the ISU 101 which on receipt enters its normal operating mode. Since the Central Server 104 may already know the bed assignment of that ISU 101 as a result of an Association process performed by the Caregiver 108 and described later, it also sends the bed assignment information to the CU 102 for that particular ISU 101. At the end of this Registration/Confirmation cycle performed by module 708, CU 102 has a table of all ISUs 101 that it is responsible for and their bed assignments which are stored as part of In-Memory Database 710.

(2) A second function of the CU 102 is to support the generation of local alerts and notifications. The Central Server 104 may send alerts generated for a specific ISU 101 to the CU 102. The Local Controller 713 receives this alert and then issues commands for to the LED 706 to flash and/or to the speaker 707 to buzz. Since the CU 102 knows the bed assignment of the ISU 101, it may display that bed number on the display 704. Once a corrective action has been taken or the status cleared by the Caretaker, the Central Server 104 notifies the CU 102 to clear the alert condition for that ISU 101. However, the pressure-time threshold settings for particular ISU may also be downloaded from the Central Server 104 to the CU 102 using the Module 712. In this instance, the local controller 713 can also generate an alert on the received measurements from a particular ISU 101 and inform the Central Server of its actions.

(3) A third function of CU 102 is to support limited but important user interactions through User Interface module 711 which supports a touch screen display 704, allowing user entry and response. This User Interface module 711 can be used by the Caregiver 108 to optionally configure the authentication, encryption, security settings for the wireless or wired local networks 705 and 702. The graphic controller 711 may display the state of the CU 102, such as network connectivity, the ISU 101 association table with the bed number, and/or notifications generated from the local controller 713. In addition, the User Interface module 711 may also selectively display the measurement data from the ISU 101 upon request by the caregiver 108.

(4) A fourth function of the CU 102 is to support the association process when a Relay Unit 111 is used by caregiver to perform the association. Here the CU 102 receives the ISU 101 ID from the Relay Unit 111 along with the Relay Unit 111 ID which it then forwards to the Central server 104. The Central Server 104 which has a record of Relay Units 111 assigned to each bed records the ISU 101 ID, and the originating CU 102 ID and then returns a confirmation message back to the CU 102 which records and forwards it to the ISU 101.

There are variants of the inventive system where the functionality of the CU 102 may be subsumed in other components or rendered unnecessary due to design preferences and/or the usage scenario. For example, in a home environment, where there might be only one patient, and where FCC might permit the use of Bluetooth (2.4 Ghz), ISU 101 may use Bluetooth to communicate with the Central Server 104 that may be implemented on the Smartphone 107. Thus the system has no need for a device like CU 102 to bridge two frequencies nor any need to track which ISUs 101 are assigned to a patient 106. Moreover, the User Interface 206 may also be implemented on the Smartphone 107 which can also be used for local alerts.

In another design preference, ISU 101 may use Wi-FI despite issues of range, form factor and battery life that it might pose. In this case ISU 101 may be able to communicate directly with the Central Server 104. Here, the frequency bridging functions of the CU 102 are not needed while other functionality can be implemented in the Central Server 104.

Battery Powered Relay Unit (RU)

Figure 10:
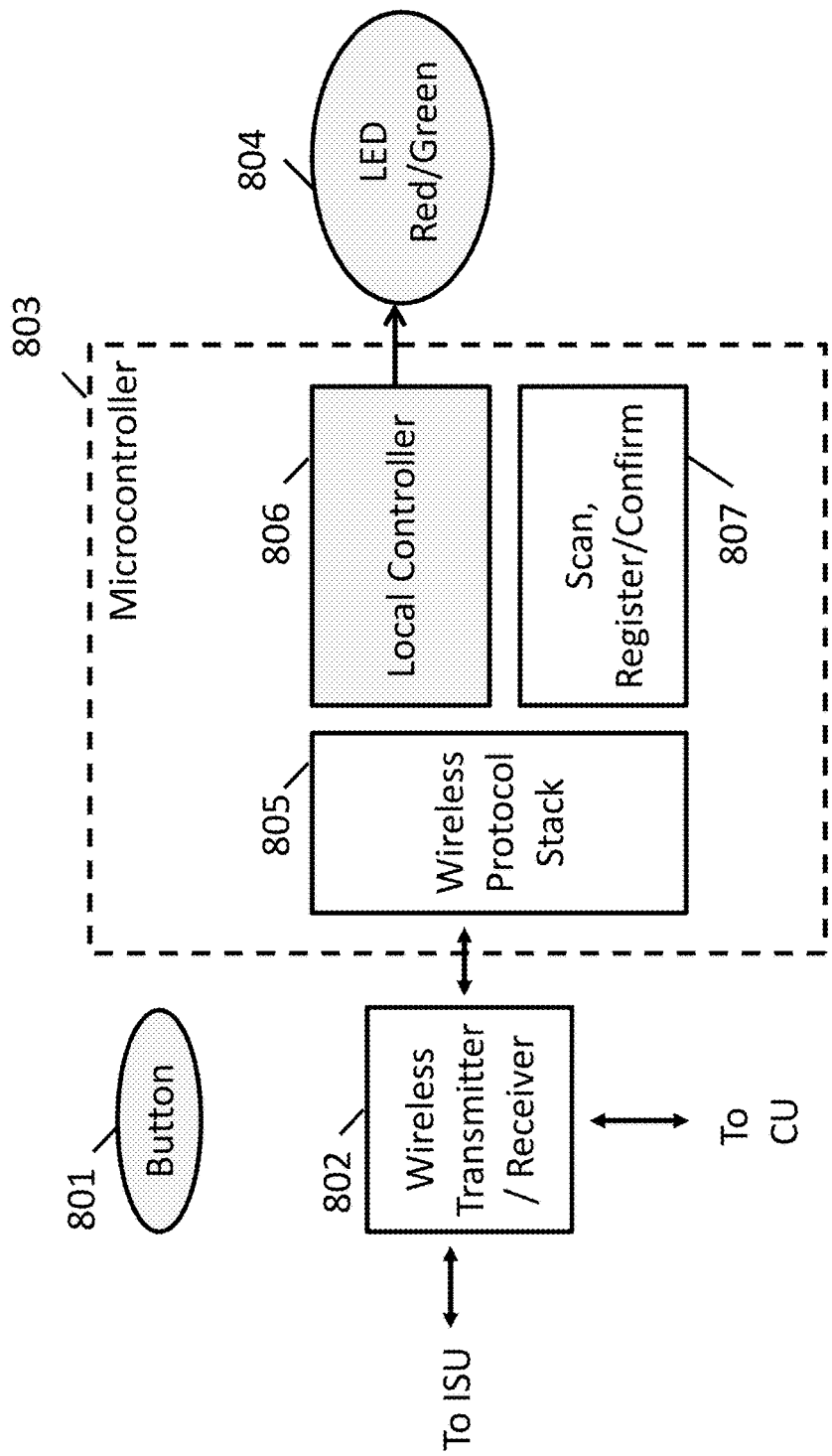
FIG. 10 illustrates the block diagram of the Relay Unit (RU)

In the instance where the Caregiver may not carry a Smartphone or Tablet with them, the optionally Battery Powered Relay Unit (RU) 111 is used for ease of associating ISU 111 with a particular bed. The RU has a short RF range of a few feet or less and is typically mounted on the patient's bed. The block diagram of the RU 111 is shown in FIG. 10. The heart of the RU 111 is the microcontroller 803 that executes the wireless protocol stack 805 and communicates with both ISU 101 and CU 102 using the same frequency spectrum. It interfaces with the Wireless Transmitter/Receiver 802 and also with LEDs 804. RU 111 is activated when the button 801 is pressed by the caregiver 108. A second pressing of the button deactivates RU 111 or RU 111 may time out to save energy when it does not scan any ISU 101 for a predetermined amount of time.

The function of the RU 111 is to listen for the ISU's 101, capture the ISU data and forward this information to the CU 102. In order to associate a particular ISU to a bed, the Caregiver 108 brings the ISU 101 in close proximity to the RU 111, activates the RU 111 and then activates all the ISUs 101. The RU 111 listen for the ISU 101 to beacon/broadcast its ID for registration. The RU 111 captures ISU beacons/broadcasts and then forwards the ISU ID and RU ID to the CU 102 for association as depicted in the Scan, Register/Confirm block 807. As the ISUs 101 are scanned by the RU 111, the caregiver 108 may receive a confirmation through the LED 804 flashing green. Once all the ISUs 101 are scanned by the RU 111 and successfully registered, the caregiver 108 may turn off the RU 111 by pressing the button 801 again or let RU 111 time out.

Analytics Engine

Figure 11:
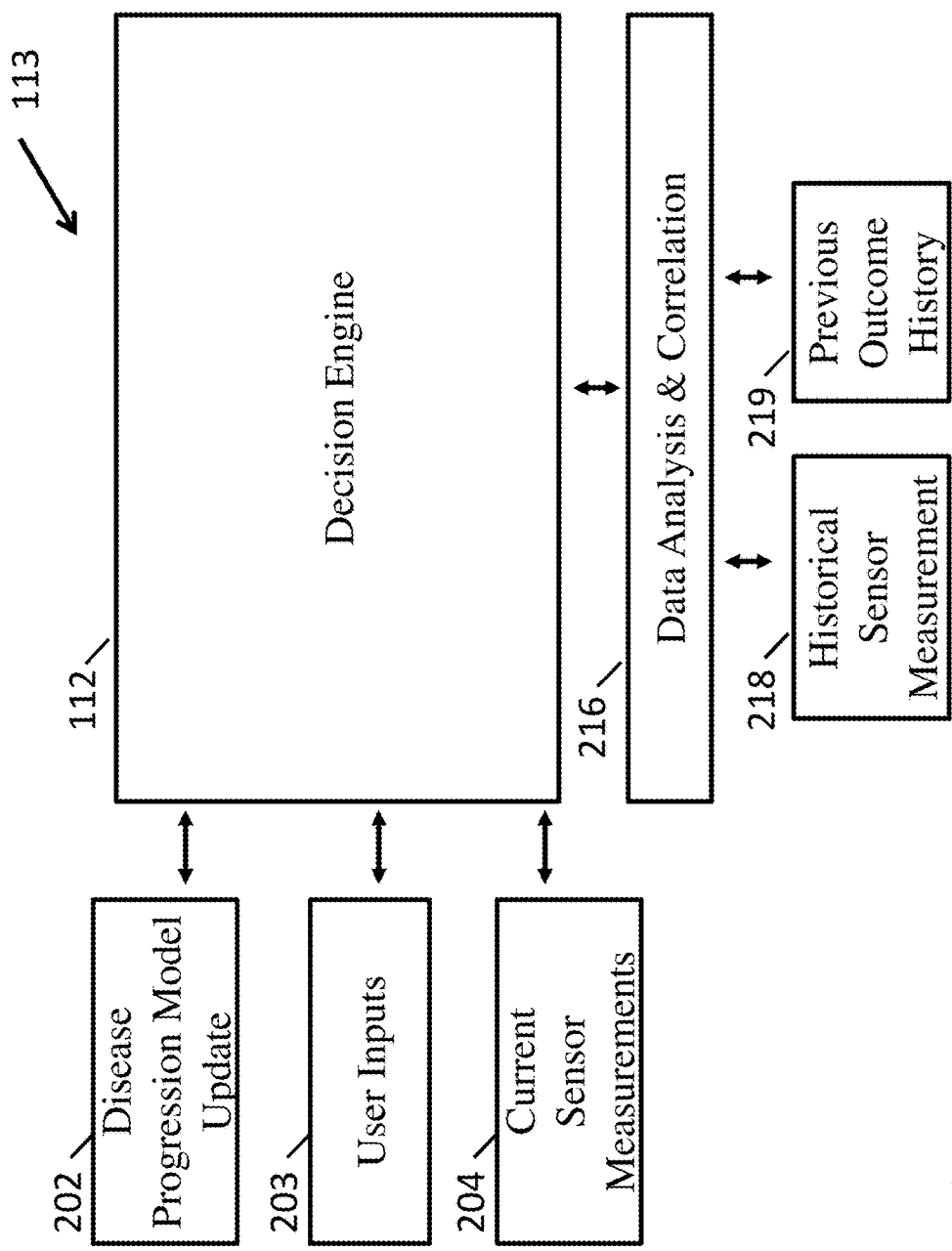
FIG. 11 describes the functional block diagram of the Analytics Engine.

FIG. 11 illustrates the block diagram of the Analytics Engine 113 which may be hosted on the Central Server 104.

The Analytics Engine 113 receives multiple inputs from users 203, measurements data 204, progression model updates 202, historical data 218, previous outcomes 219 and feeds data analysis and correlation 216 into the Decision Engine 112 to generate the alerts and notifications 209 that will be sent as a notification to the medical professionals. It may also issue control commands to the Control Module 210 to actuate corrective actions using the inflatable Mattress 211, Bed Recliner 212 or Microfluid Dispenser 213. The Decision Engine 112 implements a pressure ulcer risk predictor function using the measurements 204 from ISUs 101. In its simplest form this risk predictor function can be a simple integral based function of Pressure against Time as illustrated in FIG. 1B.

The user inputs 203 are set by the medical professionals, such as setting the threshold value on the pressure sensor data on when to generate alerts, notification and corrective actions. This is to allow flexibility for the medical professional to tailor the response to fit the patient's condition.

The Analytics Engine 113 will use the sensor measurement data 204 sent from the CU 102 as inputs into the Decision Engine 112. The measurement data 204 will be stored in the database as historical measurements 218 and will be used to generate a distribution plot, such as pressure over time for medical professionals to analyze the data for research purposes or to improve upon the techniques use to mitigate and prevent pressure ulcers.

Data analysis and correlation 216 are performed from the historical measurement data 218 and the previous outcomes 219 to determine if there are any outliers that may cause a false alert to be generated by the decision engine 112. This will enable the Decision Engine 112 to tailor the alerts and recommended actions generated and sent to the medical professionals. Data Analysis & Correlation 216 together with inputs from historical measurements 218 and their outcomes 219 are also used to continually improve the risk predictor function(s) parameters used by the Decision Engine 112.

The alerts and notifications may be sent to the HIS 105 which can then use this information to benchmark and optimize healthcare operations and patient outcomes. For example, the Affordable Care Act (ACA) provides a variety of financial incentives for healthcare systems to benchmark their performance against similar healthcare entities. The incidence of Pressure Ulcers and efforts undertaken to prevent their occurrence is one of the key benchmarks. Since the Analytics Engine 113 produces key information relating to the risks of patients getting pressure ulcers and documents alerts and actions undertaken to prevent their occurrence, the HIS 105 can now synthesize this information along with patient condition and length of stay information to establish this benchmark on an ongoing basis.

The Decision Engine 112 uses disease progression model updates 202 as an input to fine tune the decision process in generating alerts and recommended actions for the patient's medical condition. As patients' medical condition has many variables, the disease progression model updates will help in tailoring the alerts and notifications 209 to the medical professionals. For example in preventing pressure ulcers, when a patient's medical condition improves and his Braden Scale (a tool developed in 1987 by Barbara Braden and Nancy Bergstrom for assessing a patient's risk of developing a pressure ulcer) goes from high risk to low risk, the recommended action generated may be to reduce the frequency in which to turn the patient to alleviate the pressure on the body. Any alerts and notifications 209 generated are configurable by the medical professionals.

Association

Since the ISU 101 is a battery operated unit, it is important to ensure that it has a multiple year shelf life. Therefore, ISU 101 is typically activated at the time of initial use. Given that each patient 106 may have several ISUs 101 and many patients may be simultaneously monitored, it becomes critical to find a way to ensure that each ISU 101 is assigned to the right patient and the right body part.

Figure 12:
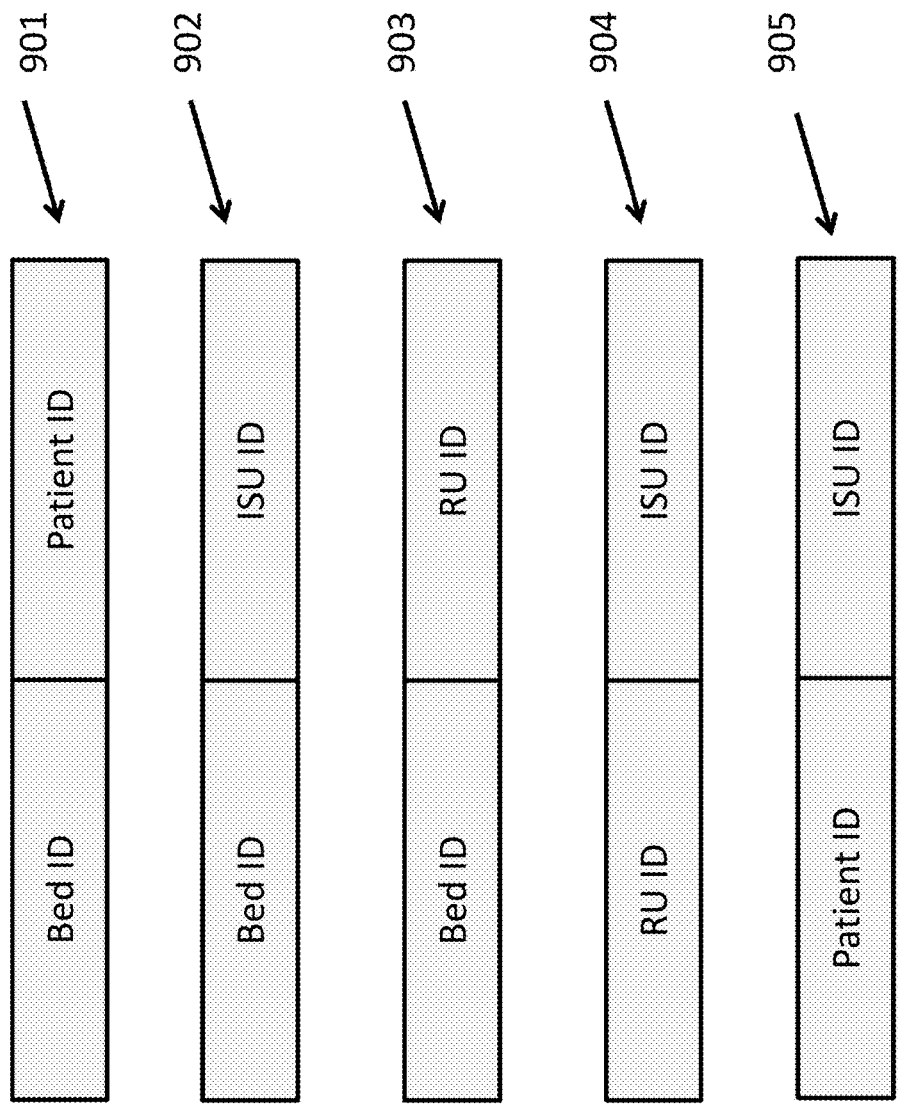
FIG. 12 illustrates the data fields used during association.

FIG. 12 shows data field type #1 901 stored in Central Server database 115 contains information about bed assignments to patients. This information is typically obtained from Healthcare Information System (HIS) 105. In the absence of the availability of this information, the patient information may be entered manually against each bed ID using UI 206.

Data Field Type #2 902 describes the data field that contains information about each ISU ID, body part ID, shape & size ID by bed ID. In general, there should be several ISU entries per Bed ID.

The ISU 101 packaging has a barcode or passive radio-frequency identification (RFID) or Near Field Communications (NFC) pattern printed on its outer packaging. In its simplest embodiment, the Caregiver 108 uses the UI 206 on their Smartphone 107 to first select the bed number and then scan the barcode or the NFC pattern on ISU 101 using their Smartphone. This populates Data Fields 902. Data field type #5 905 entries are now populated by merging entries from data fields of type #1 901 and data fields of type #2 902 and are sufficient to associate ISUs with the right patient. The caregivers may also receive confirmation that the association has been registered in the Central Server database 115.

Figure 13:
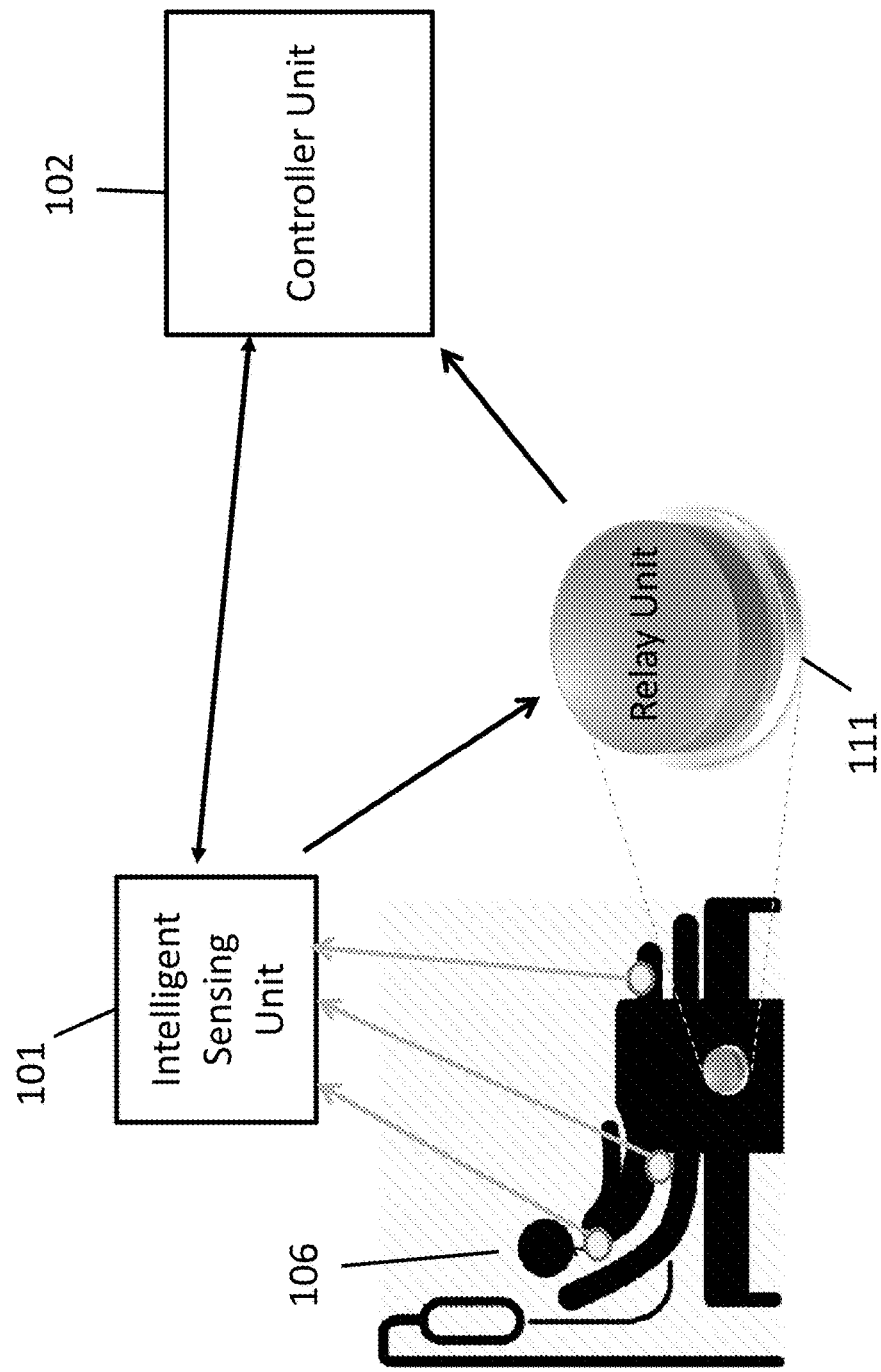
FIG. 13 depicts the use of the optional Battery Powered Relay Unit (RU) during association.

There are instances in which the Caregiver may not carry a Smartphone or tablet with them. In that scenario, the association process utilizes a battery powered Relay Unit (RU) 111 mounted on the bed FIG. 13. Each RU 111 is assigned to a particular bed as shown in data field type #3 903.

This RU 111 has a short RF range of a few feet or less. The function of the RU 111 as depicted in FIG. 12 is to listen for the ISU's 101, capture the ISU data 600 and forward this information to the CU 102. The Caregiver 108 activates RU's 111 functionality by pressing the button provided on the RU 111. In order to associate a particular ISU to a bed, the Caregiver 108 brings the ISU in close proximity to the RU, activates the RU 111 and then activates all the ISUs 101. Once all the ISUs are scanned by the RU 111, the entries in data field #4 904 are now populated and the Caregiver may press the button again to turn off the RU 111 or let the RU 111 time out. Data Field entries 901, 903, 904 can now be merged to populate Data Field entries 905.

Other Contemplated Uses of the System

Though the system has been described in detail in the context of prevention of pressure ulcers, there are a number of other applications of the system. These applications include but are not limited to the following.

Detecting if Orthopedic Casts are Too Tight

Many times, orthopedic casts end up being too tight due to imperfect design or become too tight due to swellings on the body parts after the cast is in place. Here the ISUs 101 can be put on various parts of the body before the cast is put in place. The pressures at various points inside the cast can then be monitored and alerts generated for any anomalous conditions. Here, since the user may also need to detect it at home, the system of FIG. 2 may be simplified by combining the CU 102 with a Smartphone type device into one unit. The Smartphone would then run a simplified version of the Analytics Engine as described in FIG. 11.

Detecting if a Patient is Falling Off the Bed or Attempting to Get Off the Bed

Elderly patients tend to fall off the bed. Furthermore, patients with dementia and other conditions may attempt to get off the bed in the absence of any supervision potentially harming themselves. There are special pressure mattresses available to detect the absence of the pressure which is then used to sound a local alarm. Using our system, absence of pressure in all of the ISUs may be used to detect if a patient is falling off the bed or attempting to get off the bed. Since in our system the alarm may be local or sent to a remote terminal this is a much more convenient solution for the patient and the medical staff at hand.

Tracking Patient Mobility & Location

The RF signal sent out by the ISU 101 and received by the CU 102 can be used to determine the location of the patient and the overall mobility of the patient. However, as shown in FIG. 6, the addition of an accelerometer 311 can enhance these capabilities further. Using accelerometer 311, the system can be used to detect motion at the whole body or limb level. This is potentially very useful in Early Mobility Protocols that are now at the forefront of faster healing process. Under this protocol, higher mobility of the patient or of the affected part can speed up the healing of the patient. Using this system, not only the overall mobility of the patient can be tracked but also the mobility of specific body parts, e.g. arms or legs.

Tracking Sleep Patterns

This invention can also be used to detect sleeping patterns, which would enable a medical professional to determine a wide variety of sleeping disorders such as sleep apnea, or other conditions that arise during the sleep cycle. For example, sustained pressure on fingers if they are left under the head while sleeping can cause trigger fingers or flexor tendinitis. For example, by putting an ISU 101 on the fingers the buildup of pressure can be detected and an alert sent to change the sleeping position.

Other Applications Using Other Types of Sensors within the Intelligent Sensing Unit By incorporating additional sensors such as the hydration 309 or microbial sensors 310 as part of the ISU as shown in FIG. 6 the system can also be used to detect the onset of pressure ulcers. An increase in moisture and bacterial count may be associated with the onset of pressure ulcers and other medical conditions.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A system for monitoring and preventing a patient from developing pressure ulcers, comprising:
   a. a supporting surface configured to support a body of a patient, wherein the supporting surface is divided into a plurality of compartments;
   b. a sensing unit including:
      i. a pressure sensor, attachable to a body part of a patient and having a unique identifier, the pressure sensor configured to detect strain on a skin surface of the body part exerted by the supporting surface and output pressure data indicative of pressure as a function of time applied to the skin surface of the body part based on the detected strain; and
      ii. a wireless transceiver configured to transmit the pressure data and the unique identifier;
   c. a controller unit configured to receive the pressure data and the unique identifier, associate the unique identifier with the body part of the patient, and transmit the pressure data and the unique identifier;
   d. a central server device configured to:
      i. receive the unique identifier and the pressure data from the controller unit;
      ii. determine whether the pressure data exceeds a predetermined value associated with the body part of the patient; and
      iii. transmit to the controller unit a determination that the pressure data exceeded the predetermined value, wherein the controller unit is further configured to output a signal indicative of the determination; and
   e. a control module configured to automatically control the supporting surface to lower the strain on the body part based on the pressure data until the pressure data falls below the predetermined value, wherein the control module is further configured to:
      determine a compartment of the plurality of compartments corresponding to the body part by sequentially inflating and deflating each of the compartments based on the pressure data, and identifying the compartment based on a change in the pressure data in each of the compartments; and
      control the pressure on the identified compartment to lower the strain on the corresponding body part until the pressure data falls below the predetermined value.

2. The system of claim 1, further comprising at least one of audio and visual device configured to convert the outputted signal into at least one of audio and visual alert.

3. The system of claim 1, wherein the supporting surface is a surface of an inflatable mattress.

4. The system of claim 3, wherein the inflation and deflation of the compartments is individually controlled by one or more pumps provided therein, and wherein the one or more pumps are controlled by the control module.

5. The system of claim 1, wherein the supporting surface is a surface of an angularly adjustable recliner.

6. The system of claim 5, wherein the angularly adjustable recliner is equipped with one or more controllable motors that are configured to change the inclination of the one or more sections of a bed based on the pressure data, and wherein the one or more controllable motors are controlled by the control module.

7. The system of claim 1, wherein the sensing unit further includes at least one of a microbial sensor, hydration sensor, a microbial sensor, an accelerometer, and a temperature sensor, and wherein data from the at least one of a microbial sensor, hydration sensor, a microbial sensor, an accelerometer, and a temperature sensor is transmitted to the central server device for comparison with corresponding predetermined values.

8. A computer-implemented method for monitoring and preventing a patient from developing pressure ulcers, comprising the steps of:
   a. detecting, by a sensing unit attachable to a body part of a patient, strain on a skin surface of the body part exerted by a supporting surface, wherein the supporting surface is divided into a plurality of compartments;
   b. identifying the sensing unit with a unique identifier;
   c. associating the unique identifier with the body part of a patient and the pressure data;
   d. wirelessly transmitting by the sensing unit the unique identifier and pressure data indicative of the pressure as a function of time applied to the skin surface of the body part based on the detected strain;
   e. receiving by a central server the pressure data associated with the body part of a patient;
   f. comparing by the central server the pressure data with a predetermined value associated with the body part of the patient;
   g. outputting by the central server a signal when the pressure data exceeded a predetermined value; and
   h. automatically controlling by the control module, the supporting surface to reduce the strain on the body part based on the pressure data until the pressure data falls below the predetermined value;
   i. determining by the control module, a compartment of the plurality of compartments corresponding to the body part by sequentially inflating and deflating each of the compartments based on the pressure data, and identifying the compartment based on a change in the pressure data for each of the compartments; and
   j. controlling by the control module, the pressure on the identified compartment to lower the strain on the corresponding body part until the pressure data falls below the predetermined value.

9. The method of claim 8, wherein the outputted signal is at least one of audio and visual alert.

10. The method of claim 8, further comprising the step of measuring the body part using at least one of a microbial sensor, hydration sensor, a microbial sensor, an accelerometer, and a temperature sensor.

11. A system for monitoring and preventing a patient from developing pressure ulcers, comprising:
   a. a supporting surface for supporting a body of a patient, wherein the supporting surface is divided into a plurality of compartments;
   b. a sensing unit including:
      i. a pressure sensor, attachable to a body part of a patient and having a unique identifier, the pressure sensor configured to detect strain on a skin surface of the body part exerted by the supporting surface and output pressure data indicative of pressure as a function of time applied to the skin surface of the body part based on the detected strain; and
      ii. a wireless transceiver configured to transmit the pressure data and the unique identifier;
   c. a central server device configured to:
      i. receive the unique identifier and the pressure data from the sensing unit;
      ii. associate the unique identifier with the body part of the patient;
      iii. determine whether the pressure data exceeds a predetermined value associated with the body part of the patient; and
      iv. transmit a determination that the pressure data exceeded the predetermined value;
   d. a mobile device configured for receiving the determination that the pressure data exceeded the predetermined value; and
   e. a control module configured to automatically control the supporting surface to lower the strain on the body part based on the pressure data until the pressure data falls below the predetermined value, wherein the control module is further configured to:
   determine a compartment of the plurality of compartments corresponding to the body part by sequentially inflating and deflating each of the compartments based on the pressure data, and identifying the compartment based on a change in the pressure data for each of the compartments; and
   control the pressure on the identified compartment to lower the strain on the corresponding body part until the pressure data falls below the predetermined value.

12. The system of claim 11, wherein the mobile device outputs a signal indicative of the determination.

13. The system of claim 11, wherein the supporting surface is a surface of an inflatable mattress.

14. The system of claim 11, wherein the supporting surface is a surface of an angularly adjustable recliner.

15. The system of claim 12, further comprising at least one of audio and visual device for converting the outputted signal into at least one of audio and visual alert.

* * * * *